United States Patent
Janowski et al.

(10) Patent No.: US 8,172,876 B2
(45) Date of Patent: May 8, 2012

(54) SPINAL FIXATION SYSTEMS

(75) Inventors: Brian P. Janowski, Marquette, MI (US); Francis J. Korhonen, Neguanee, MI (US); Thomas S. Kilpela, Marquette, MI (US); Gregory Berrevoets, Skandia, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 889 days.

(21) Appl. No.: 12/067,616

(22) PCT Filed: Sep. 20, 2006

(86) PCT No.: PCT/US2006/036856
§ 371 (c)(1),
(2), (4) Date: Jul. 31, 2008

(87) PCT Pub. No.: WO2007/035884
PCT Pub. Date: Mar. 29, 2007

(65) Prior Publication Data
US 2009/0030457 A1    Jan. 29, 2009

Related U.S. Application Data

(63) Continuation-in-part of application No. 10/358,530, filed on Feb. 5, 2003, now Pat. No. 7,141,051.

(60) Provisional application No. 60/718,975, filed on Sep. 20, 2005, provisional application No. 60/720,955, filed on Sep. 26, 2005.

(51) Int. Cl.
*A61B 17/70* (2006.01)

(52) U.S. Cl. ...................................... 606/246

(58) Field of Classification Search .................. 606/246, 606/264–270, 272, 278, 301, 305, 308; 411/393; 403/362
See application file for complete search history.

(56) References Cited

U.S. PATENT DOCUMENTS

| 5,330,473 | A | * | 7/1994 | Howland | 606/250 |
| 5,380,326 | A | * | 1/1995 | Lin | 606/330 |
| 5,443,467 | A | * | 8/1995 | Biedermann et al. | 606/65 |
| 6,077,262 | A | * | 6/2000 | Schlapfer et al. | 606/305 |
| 6,660,004 | B2 | * | 12/2003 | Barker et al. | 606/328 |
| 6,755,829 | B1 | * | 6/2004 | Bono et al. | 606/308 |
| 6,837,889 | B2 | * | 1/2005 | Shluzas | 606/270 |
| 2004/0260284 | A1 | * | 12/2004 | Parker | 606/61 |

* cited by examiner

*Primary Examiner* — Thomas J Sweet
*Assistant Examiner* — David Comstock
(74) *Attorney, Agent, or Firm* — Fitch, Even, Tabin & Flannery, LLP

(57) ABSTRACT

A spinal fixation system is provided that includes a coupling member and a locking device that is operable to fix an elongate member relative to the coupling member. In one form, locking device includes opposing lock arms operable to retain the locking device relative to the coupling member in an initial position prior to the locking device fixing the elongate member relative to the coupling member. In another form, the coupling member and locking device include cooperating structure therebetween in the form of a protrusion and a guide track, the cooperating structure arranged and configured to retain the locking device within an internal space of the coupling member. There is also provided a retainer operable to minimize pivoting of the coupling member relative to an anchor member and to substantially retain an anchor member depressed within an internal space of the coupling member to minimize play therebetween.

11 Claims, 34 Drawing Sheets

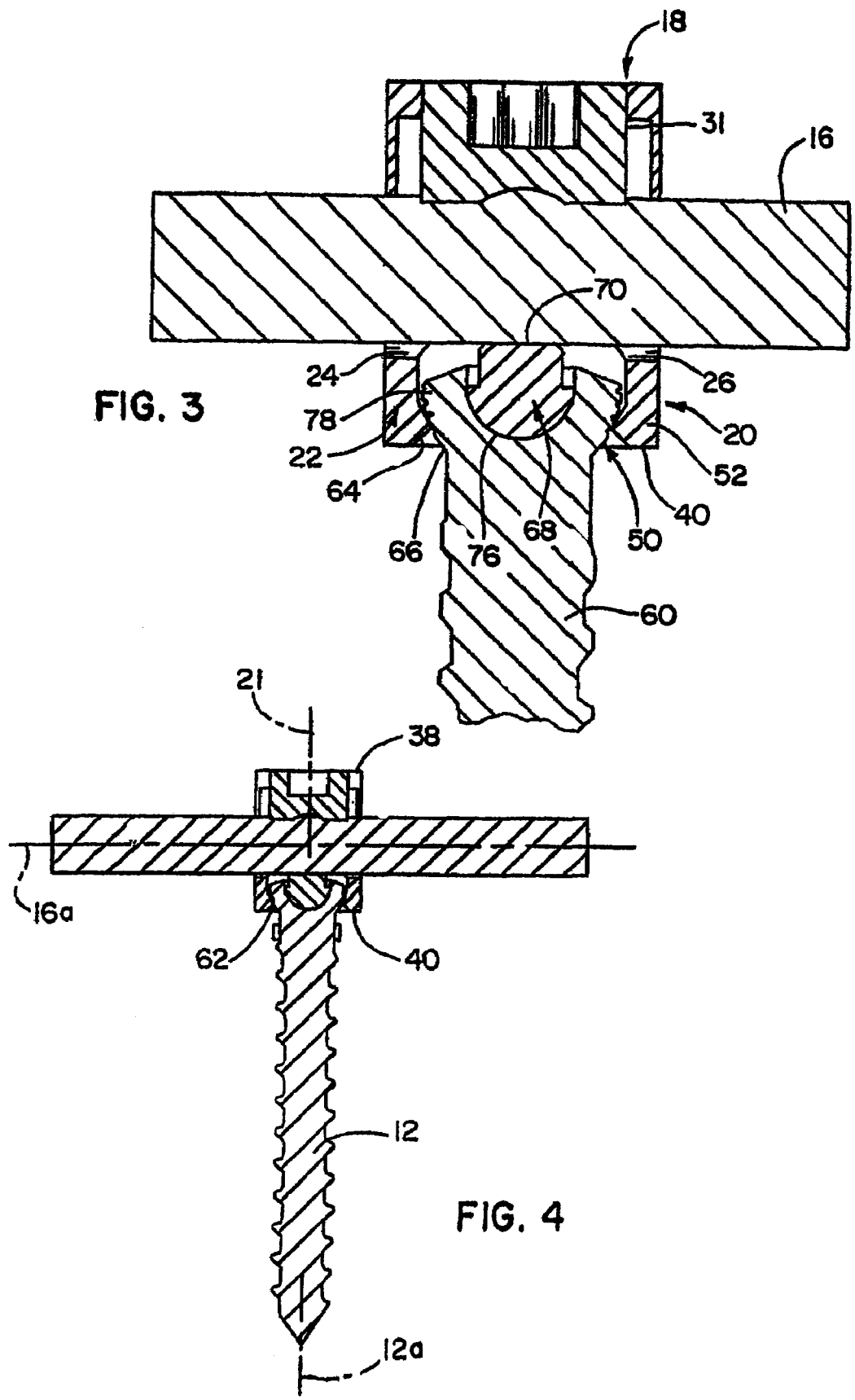

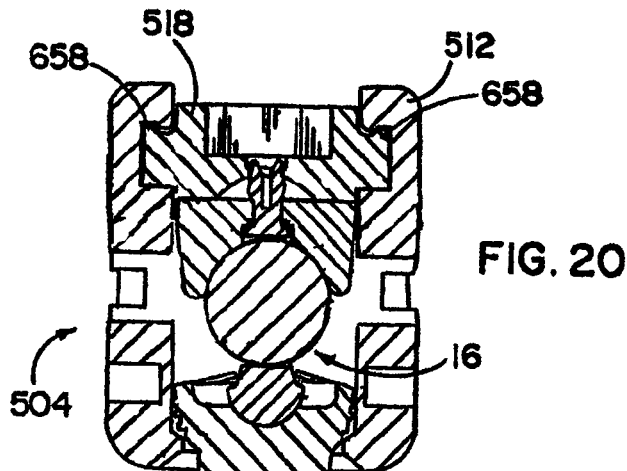
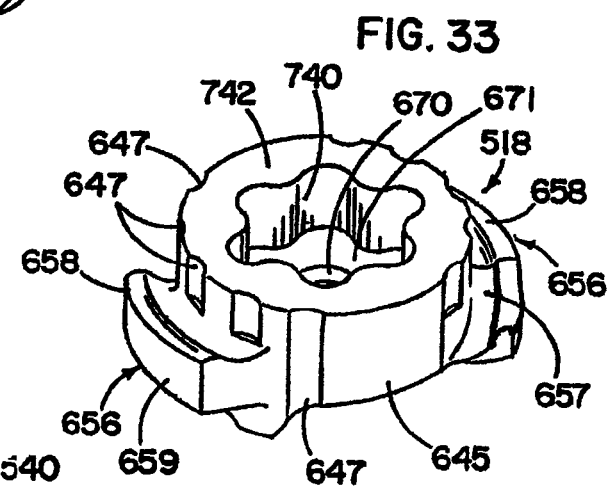
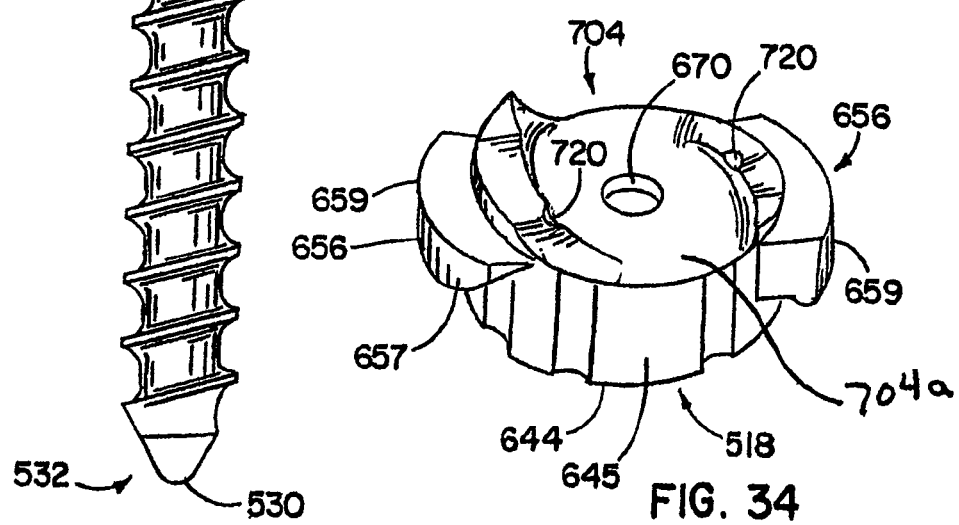
FIG. 20
FIG. 33
FIG. 34

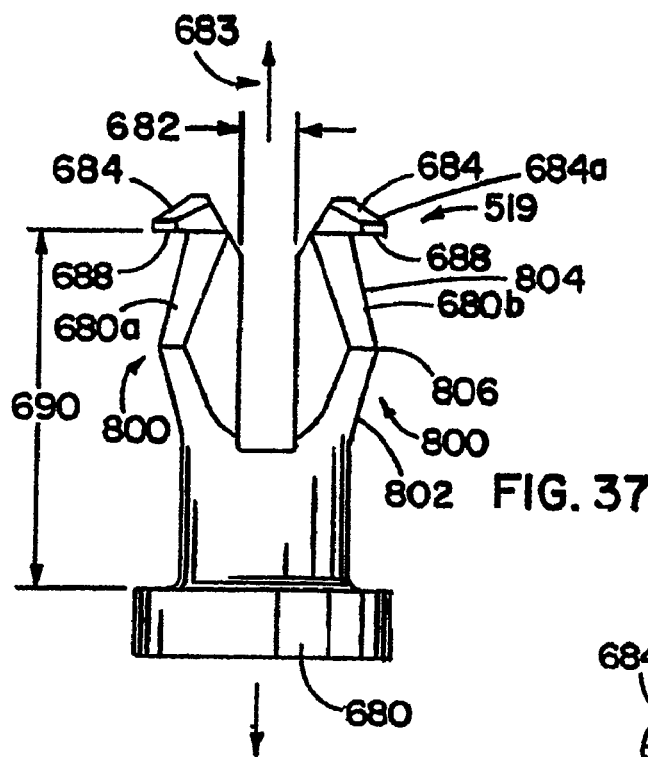
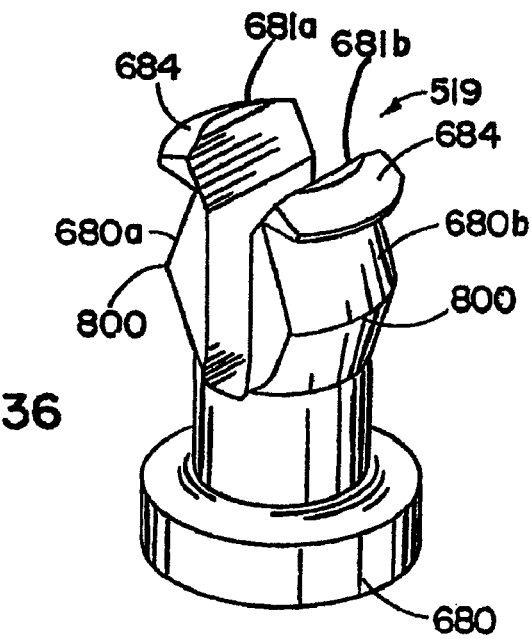
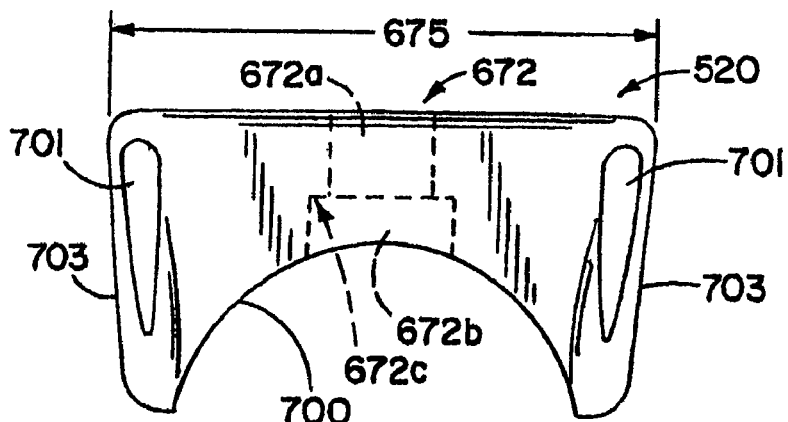
FIG. 37
FIG. 36
FIG. 38

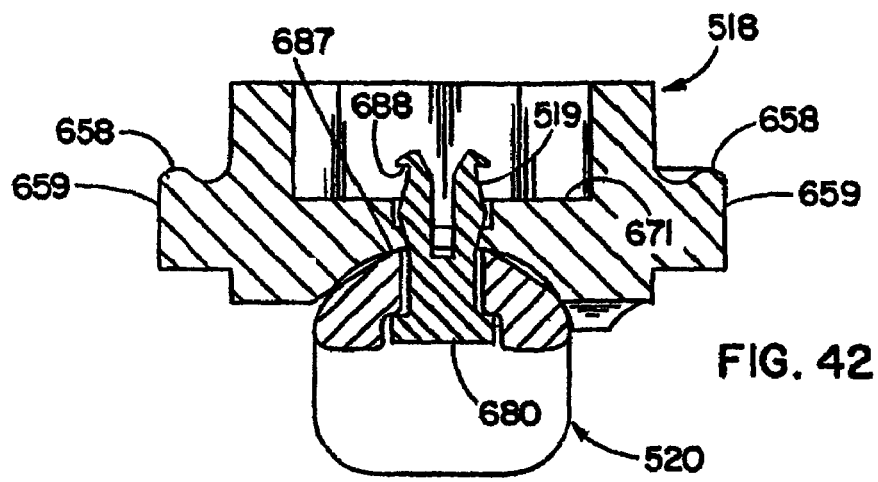
FIG. 42
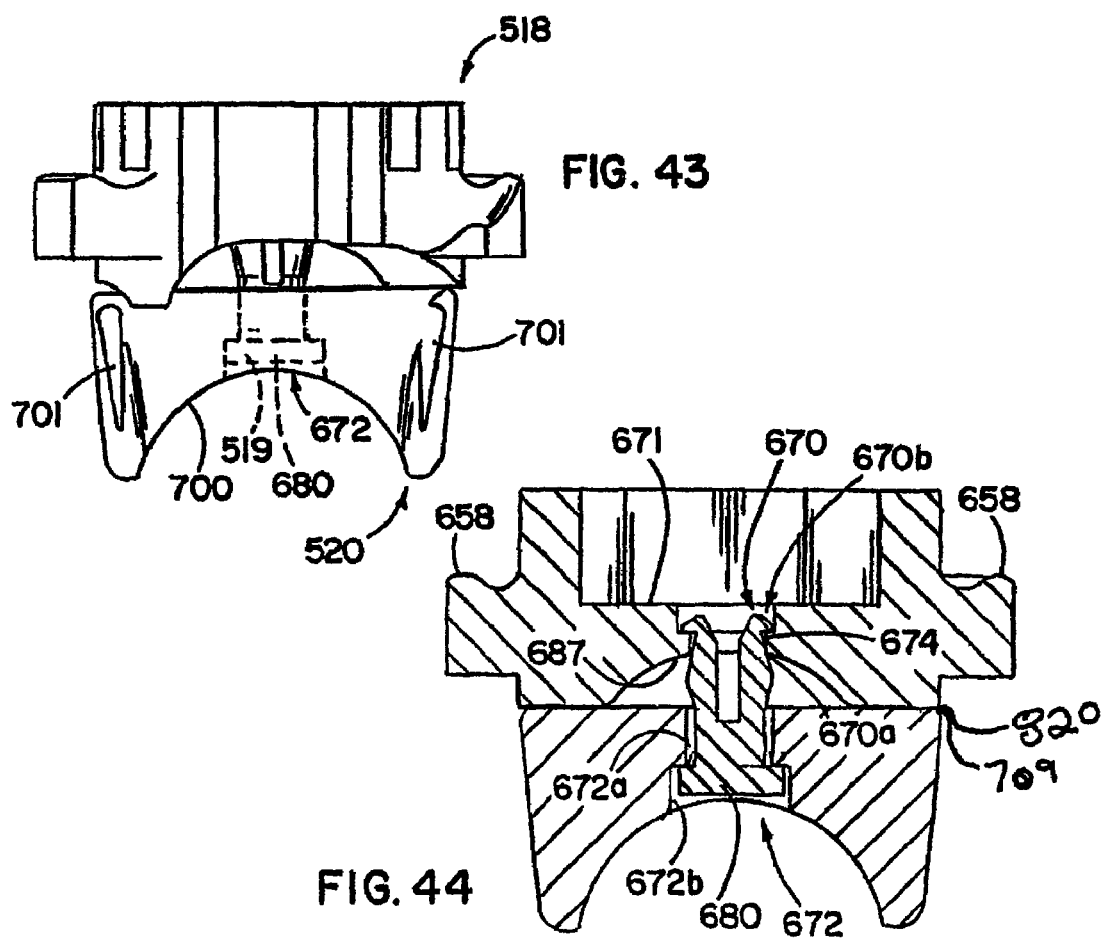
FIG. 43
FIG. 44

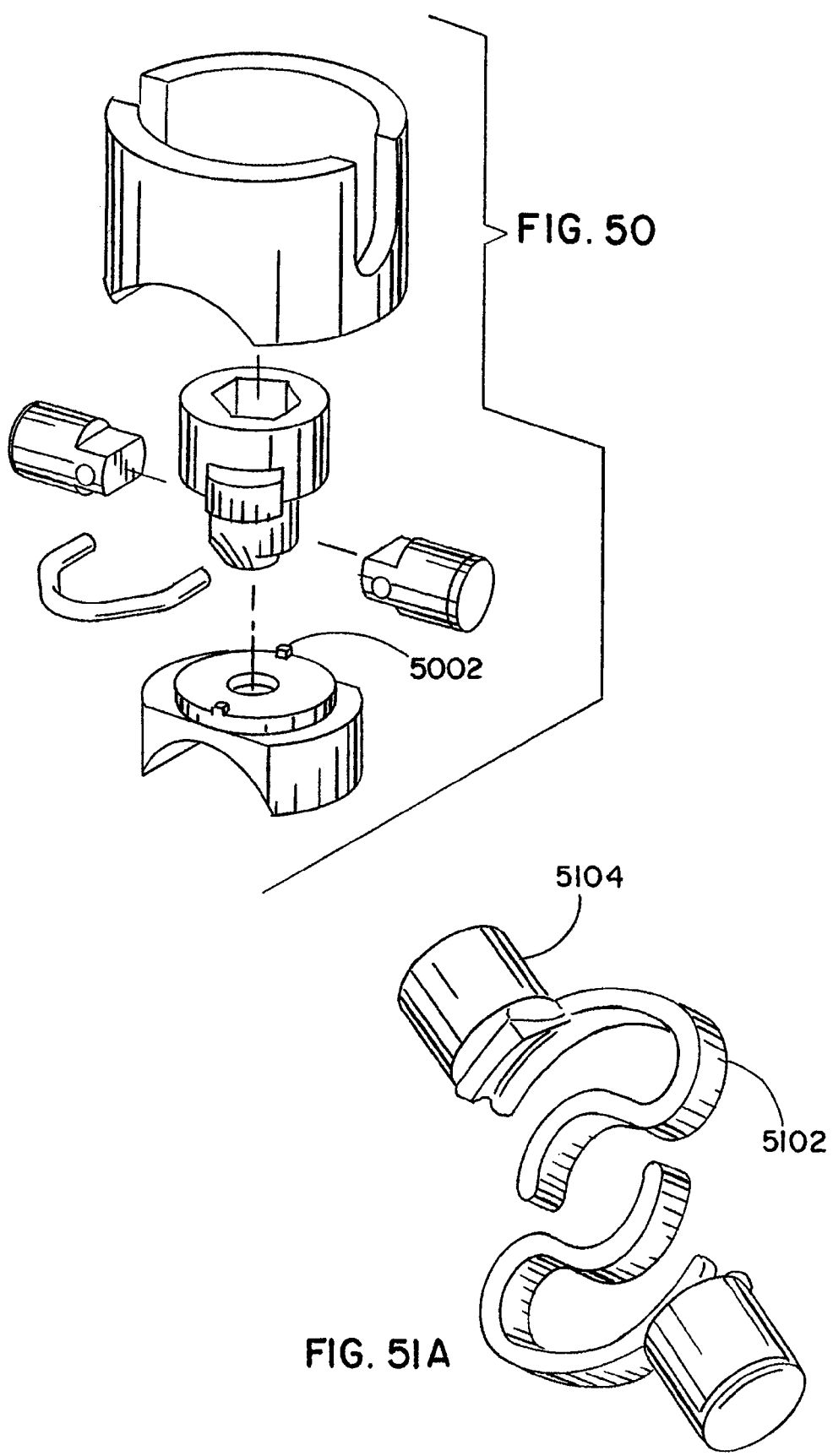

SPINAL FIXATION SYSTEMS

CROSS-REFERENCE TO RELATED APPLICATION

This application claims benefit of U.S. Provisional Application No. 60/718,975, filed Sep. 20, 2005, and U.S. Provisional Application No. 60/720,955, filed Sep. 26, 2005, which are hereby incorporated herein by reference in their entirety. This application is also a continuation-in-part of prior U.S. application Ser. No. 10/358,530, filed, Feb. 5, 2003, now U.S. Pat. No. 7,141,051 B2, which is hereby incorporated herein by reference in its entirety.

FIELD OF THE INVENTION

The invention relates to spinal fixation systems and, more particularly, to polyaxial spinal fixation systems.

BACKGROUND OF THE INVENTION

Spinal rods for immobilizing vertebral bones of the spinal column are typically anchored to the vertebrae via bone screws that extend through the pedicle into the vertebral bodies or by hooks that engage about the vertebrae. The rods are connected to the anchor members by generally yoke-shaped couplers that can be either integral with the anchor member head or separate components from the anchor member for use in polyaxial pedicle screw systems for spinal rod fixation. These prior systems employ some sort of compression member that is brought down into engagement either directly or indirectly with the spinal rod for securing it relative to the anchor member, and in polyaxial systems for securing the anchor member relative to the coupler.

For this purpose, the compression member and coupler typically are engaged via threading therebetween such that the compression member is threaded down into its locked position in or about the yoke-shaped coupler. Alternatively, wedge cam surfaces between radial flanges on the compression member and radial recesses in the coupler walls have also been employed to advance the compression member for pushing the spinal rod down into fixed position relative to the screw anchor member, see U.S. Pat. No. 6,565,565, to Yuan, et al. The problem with the threaded or cam wedge systems of spinal rod locking is that to allow the compression member to advance relative to the coupler, the size or profile of the coupler as well as the compression member necessarily is increased. In other words, to have threads or cam surfaces formed on the coupler requires that the walls be provided with a sufficient axial extent for the advancement of the threaded or cammed compression member therealong. Additionally, many systems utilize a full spherical head on a bone screw located adjacent the rod, thereby requiring a greater coupler to capture the rod and the bone screw head.

In polyaxial spinal fixation systems, the use of inserts between the head of the anchor member and the spinal rod has been proposed, see U.S. Pat. No. 5,733,286 to Errico, et al. The large hemispherical insert of Errico, et al. is engaged on a concave recess formed in a screw head received in the coupler allowing the coupler to adjust relative to the polyaxial-pedicle screw for receipt of the spinal rod in its desired position.

However, the entire Errico, et al. system has an undesirably large profile as it employs a threaded set screw for clamping on the spinal rod, and the hemispherical insert extends well beyond the top of the screw head into the coupler channel through which the spinal rod is received.

SUMMARY OF THE INVENTION

In accordance with the present invention, a low-profile spinal fixation system is provided. In one aspect, a cam lock member of a coupling device is fixed against translation as it is turned so that a cam surface of the lock member causes an elongate member that extends generally along the spinal column, e.g., spinal rod, to be forced or pushed downward. As the cam lock member does not translate along the coupling device, the size of the coupling device can be kept to a minimum. Further, the low profile of the present system may allow for minimally invasive surgical procedures to be employed therewith such as with the components thereof being cannulated for use with a guide wire.

In another aspect, a polyaxial spinal fixation system is provided having a coupling member including an internal seat surface and a central bore sized to allow the anchor member to extend through the bore in several different orientations. The anchor member includes a head having an upper recess in which a low profile insert is provided. In a preferred form, the insert has an upper surface that is substantially flat. Other alternatives for the insert including the upper surface thereof are that the insert may or may not deform when compressed, the insert upper surface may have radially oriented concave paths or valleys so that the insert rotates to the closest path to meet with the spinal rod, or the insert may have a cup or peripheral ridge that deforms when compressed by the spinal rod to form a path without deforming the spinal rod. The upper surface is fit in the head recess with the insert sized so that the upper surface projects only slightly beyond the proximal end of the anchor member to keep the profile of the insert to a minimum. In one form, the insert upper surface is sized from the interface with the head recess at the bottom of the insert so that even with the anchor member pivoted to its maximum extent relative to the coupling member, the insert upper surface still projects slightly beyond the upper end of the anchor member head, e.g., by approximately 0.010 inch.

In a preferred form, the insert has an enlarged lower portion having a lower arcuate surface thereon for bearing against the concave recess surface of the anchor member head, and a central projection that extends upwardly from the lower portion and includes the flat upper surface thereon. The anchor member head preferably includes a retainer such as in the form of staked portions that allow the insert to self-adjust as the angle of the coupling member is adjusted with the flat surface projecting above the anchor member head for engaging the spinal rod.

In another preferred form, the cam member cooperates with a saddle or clamping member disposed between the cam member and the spinal rod. Upon turning of the cam member to lock the spinal rod, the cam member does not move axially along the coupling member but instead cams against the saddle member driving it axially toward the spinal rod until the spinal rod is secured between the clamping member and the insert. The cam member preferably is secured in assembly to the clamping member with a connector in the form of a dual-pronged spring clip so that the cam member stays assembled with the clamping member during a surgical procedure.

BRIEF DESCRIPTION OF THE DRAWINGS

FIG. 3 is a cross-sectional view of the spinal fixation system showing a recess formed in the screw head in which a low profile anvil insert is received for clamping of the spinal rod thereagainst;

FIG. 4 is a cross-sectional view similar to FIG. 3 showing the relative sizes of the various components of the spinal fixation system;

FIG. 20 is a side elevation view partially in section of the system of FIG. 19 in a locked position showing a spinal rod secured between the clamping and insert members;

FIG. 33 is a perspective view of the cam lock member of FIG. 19;

FIG. 34 is a bottom perspective view of the cam lock member showing a programmed cam surface at the bottom thereof;

FIG. 36 is a perspective view of the spring clip connector of FIG. 19 showing a pair of resilient prongs;

FIG. 37 is a side elevation view of the connector showing the spacing of the prongs and the flanged free ends thereof;

FIG. 38 is a side view of the clamping member of FIG. 19;

FIG. 42 is a cross-sectional view similar to FIG. 41 showing the spring clip connector with the flanged ends of the clip prongs spaced from the cap member;

FIG. 43 is a side elevation view of the cam lock member and the clamping member in a locked position relative to the spinal rod;

FIG. 44 is a cross-sectional view similar to FIG. 43 showing the clamping member shifted down along with the spring clip connector with the cap member axially fixed and rotated to its locked position;

FIG. 50 is a further exploded perspective view of FIG. 47 illustrating greater detail of the assembly;

FIG. 51A is a perspective view of an alternate method of biasing the cam bars;

DETAILED DESCRIPTION OF THE PREFERRED EMBODIMENTS

Figure 1:
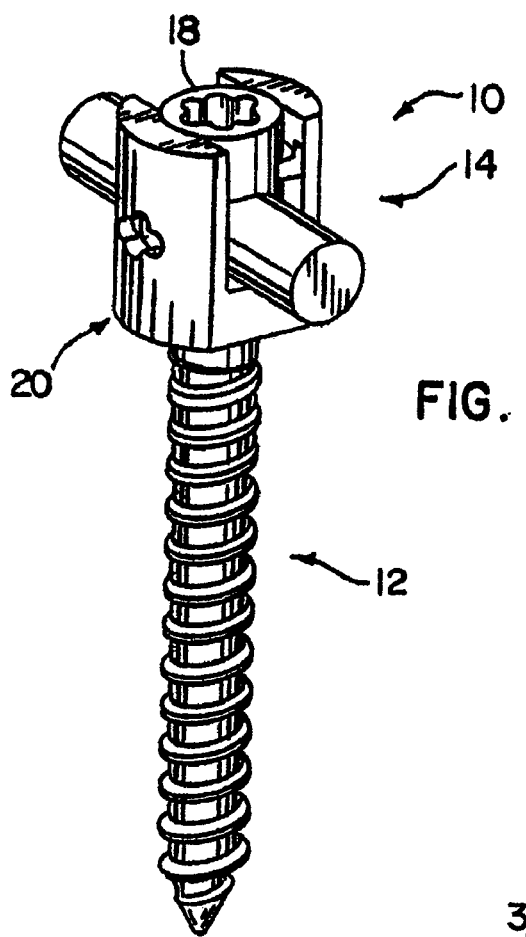
FIG. 1 is a perspective view of a first form of the spinal fixation system in accordance with the present invention showing a bone screw and a coupling device including a coupling member and a cam lock member for securing a spinal rod relative to the bone screw.
Figure 2:
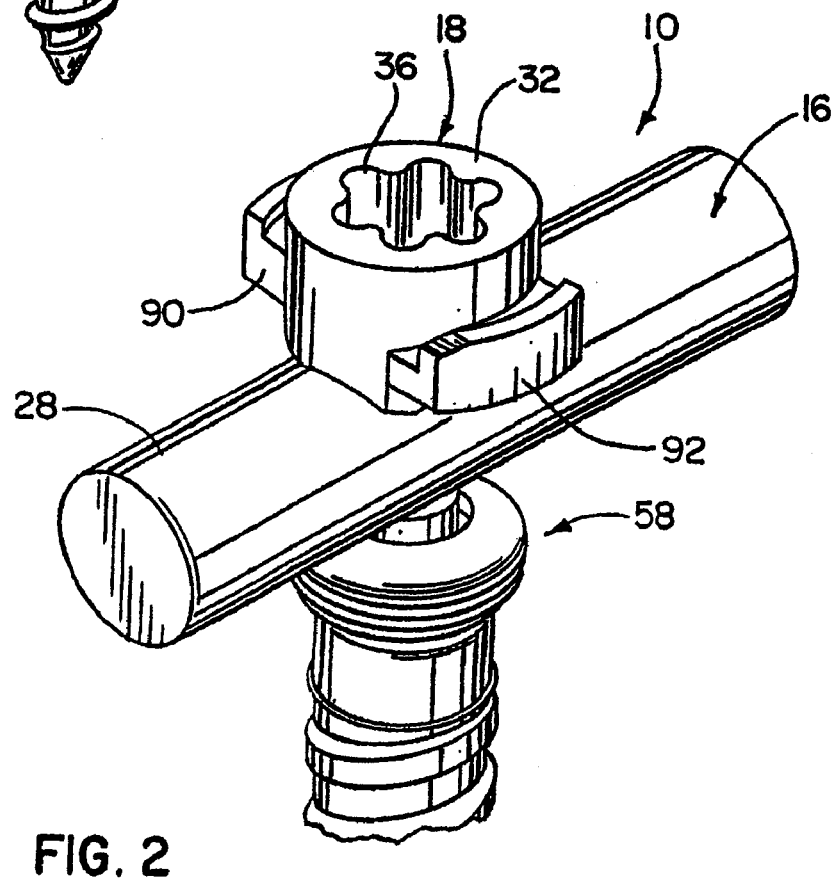
FIG. 2 is an enlarged perspective view of the spinal fixation system of FIG. 1 with the coupling member removed to better illustrate the cam lock member and to show the configuration of the head of the bone screw.

In FIGS. 1 and 2, a low profile spinal fixation system 10 in accordance with one form of the present invention is depicted. As shown, the spinal fixation system 10 includes a bone anchor member in the form of a bone screw 12 and a coupling device generally designated 14. The coupling device 14 is operable to secure an elongate member in the form of spinal rod 16 in place relative to the bone screw 12. The coupling device 14 includes a compression or cam lock member 18 and a coupling member 20, which cooperate to secure the spinal rod 16 relative to the bone screw 12 anchored in a vertebral bone with the rod 16 generally extending axially along the spinal column. The coupling device 14 and specifically the cam lock member 18 and coupling member 20 are provided with a compact configuration. In particular, the cam lock member 18 and coupling member 20 are provided with a very low profile in a direction indicated by axis line 21 extending transverse and specifically orthogonally to the axis 16a of the spinal rod 16 fixed relative to the bone screw 12 by the coupling device 14, as best seen in FIG. 4.

More specifically, the low profile of the coupling device 14 is obtained by having the cam lock member 18 be effective to lock the spinal rod 16 without the need to advance the cam lock member 18 along the coupling member 20. In this regard, the coupling member 20 can be provided with a body 22 having side openings 24 and 26 through which the spinal rod 16 passes with the body 22 free of any threading or cam surfaces that cooperate with the cam lock member 18 for locking of the spinal rod 16 relative to the bone screw 12. Instead, the cam lock member 18 is fixed against translation relative to the coupling member 20, and preferably cooperates with the outer curved surface 28 of the rod 16 itself to secure it in position relative to the screw 12 in the system 10.

Figure 8:
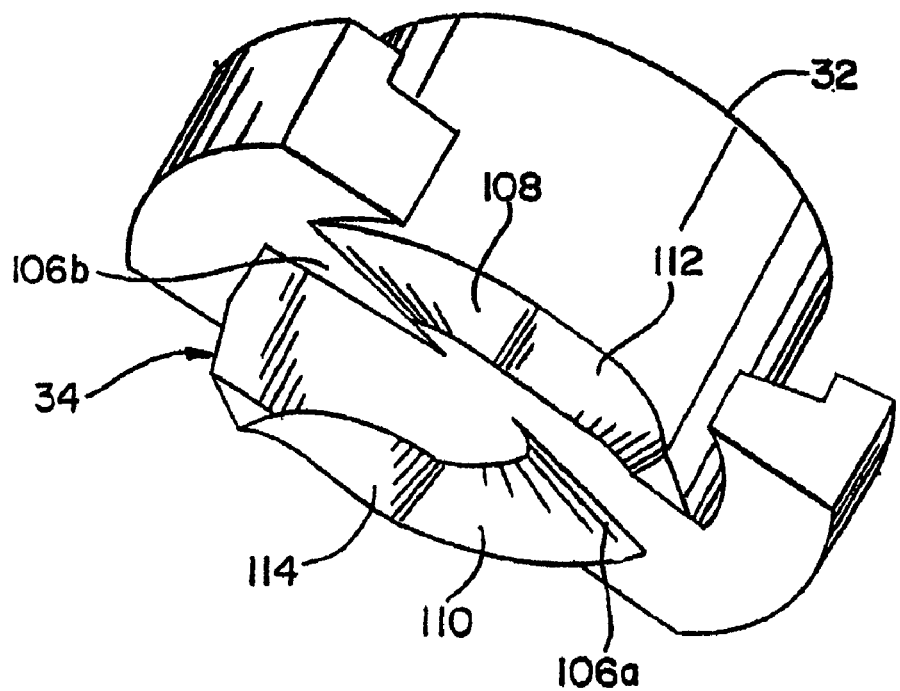
Figure 9:
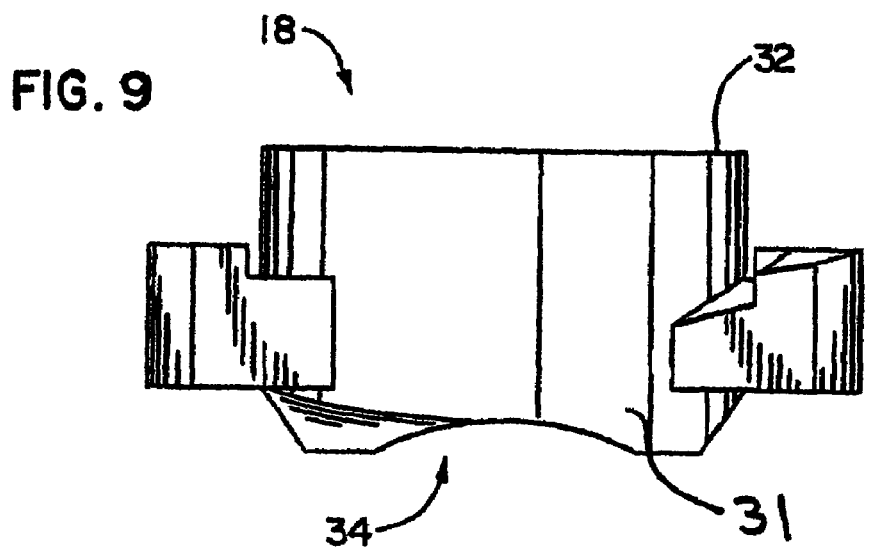
Figure 10:
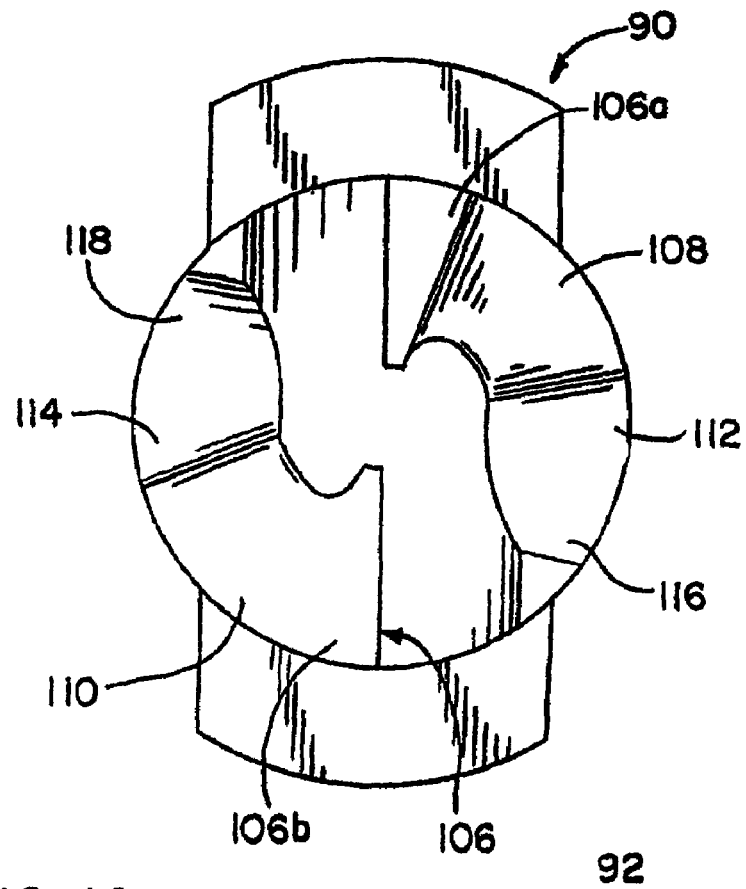

For this purpose, the cam lock member 18 has a generally annularly configured body 30 having a very short axial extent along its turning axis 21 thereof via annular side surface 31 extending between its top and bottom surfaces 32 and 34. The top surface 32 is provided with driving surface portions 36 which cooperate to form a predetermined configuration for the receipt of a similarly configured drive tool for turning the cap member 18 between unlocked and locked positions thereof. The bottom surface 34 is programmed or contoured to provide a camming action on the curved surface 28 of the rod 16 when the cam lock member 18 is turned, as best seen in FIGS. 8 and 10 and as will be described more fully hereinafter.

Figure 16:
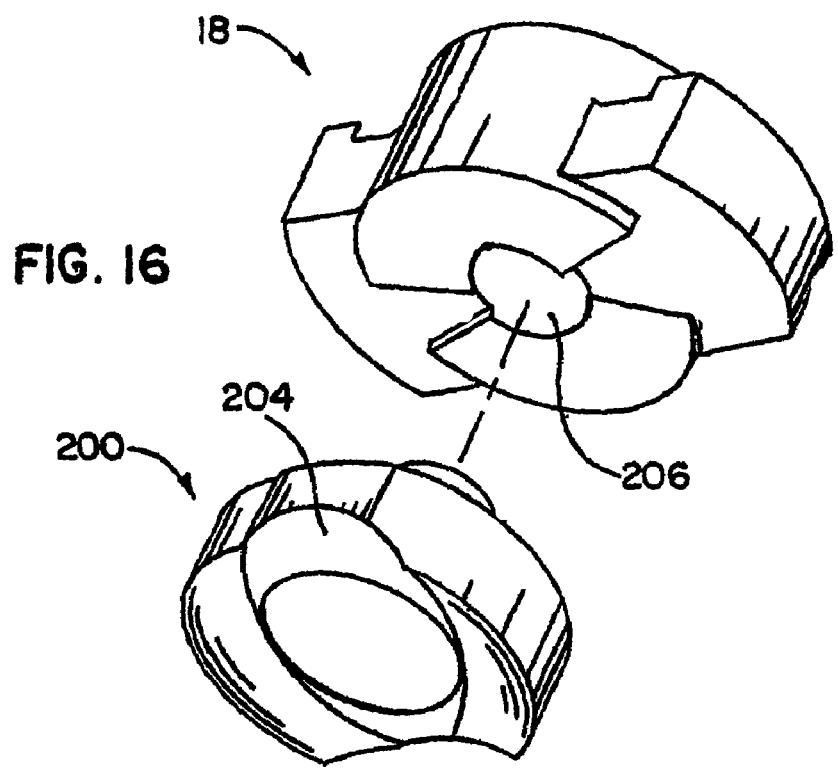
FIGS. 16-18 are various views of alternative camming system employing both a cam lock member and a saddle member.
Figure 17:
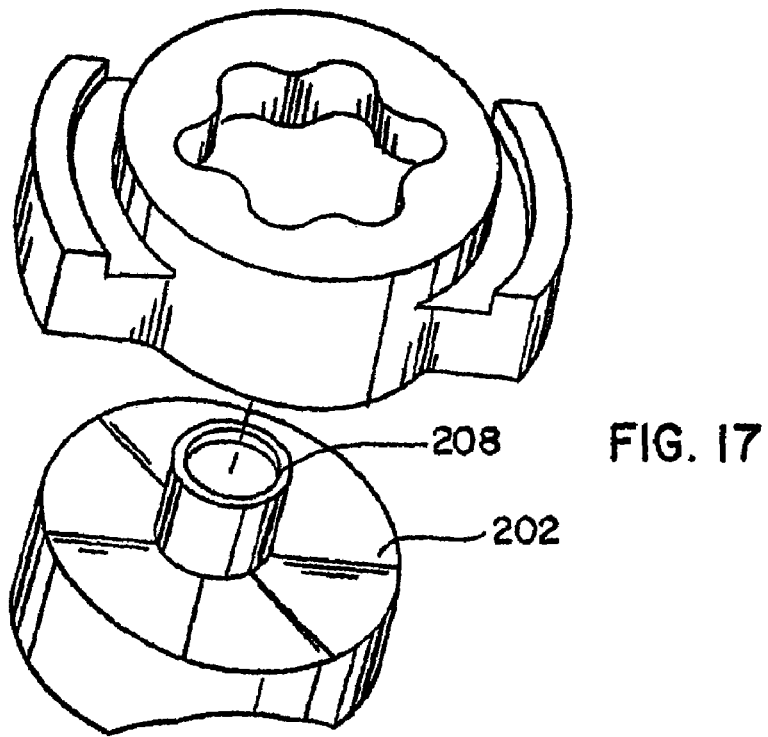
Figure 18:
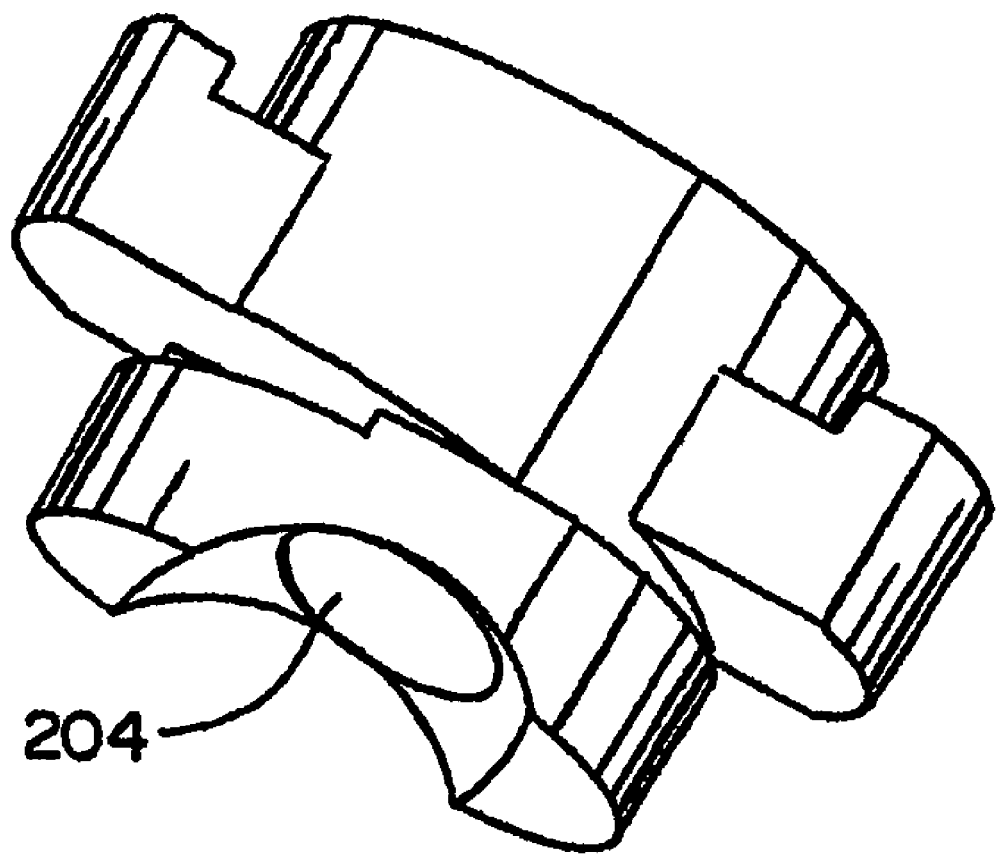

Although less preferred in terms of maintaining a low profile for the spinal fixation system 10 herein, an intermediate clamping member in the form of saddle member 200 can be provided between the lock member 18 and spinal rod 16, as shown in FIGS. 16-18. The saddle member 200 has an upper cam surface 202 configured for cooperation with lock member cam surface 34 when the lock member 18 is turned to its locked position so that the saddle member 200 shifts downwardly along axis 21 for clamping against the rod 16. The saddle member is provided with a curved bottom surface 204 which substantially matches the curvature of rod surface 28 so that the saddle member 200 engages and pushes against the rod 16 without camming thereagainst. The cam lock member 18 can include a center opening 206 which receives a central post 208 projecting upward from the saddle member 200 to keep the cam lock member 18 and saddle member 200 oriented properly with respect to each other.

Figure 11:
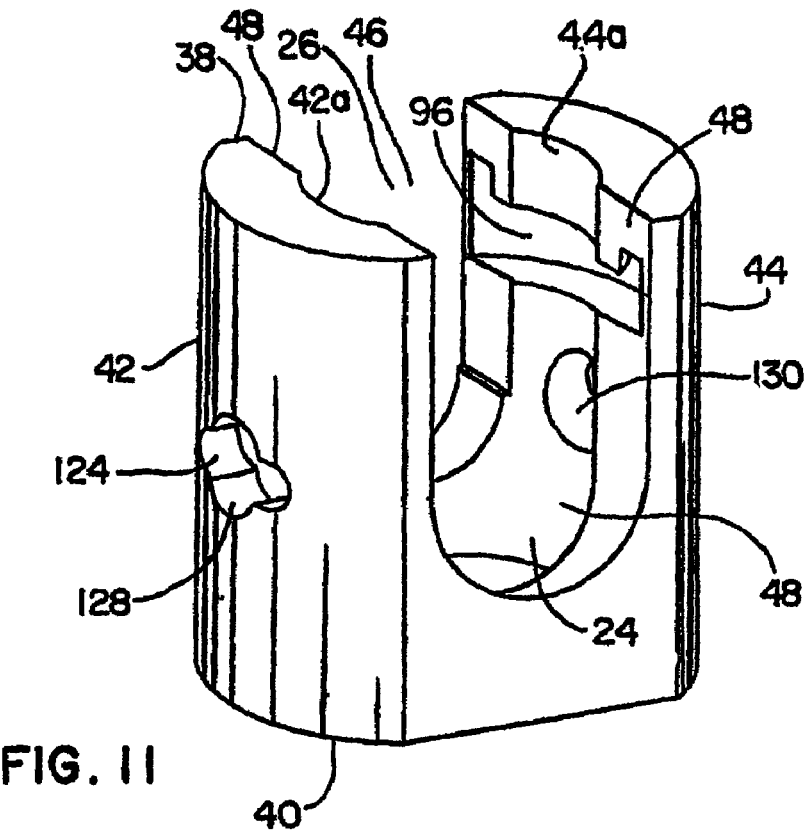
FIGS. 11-13 are various views of the yoke-shaped coupling member.
Figure 12:
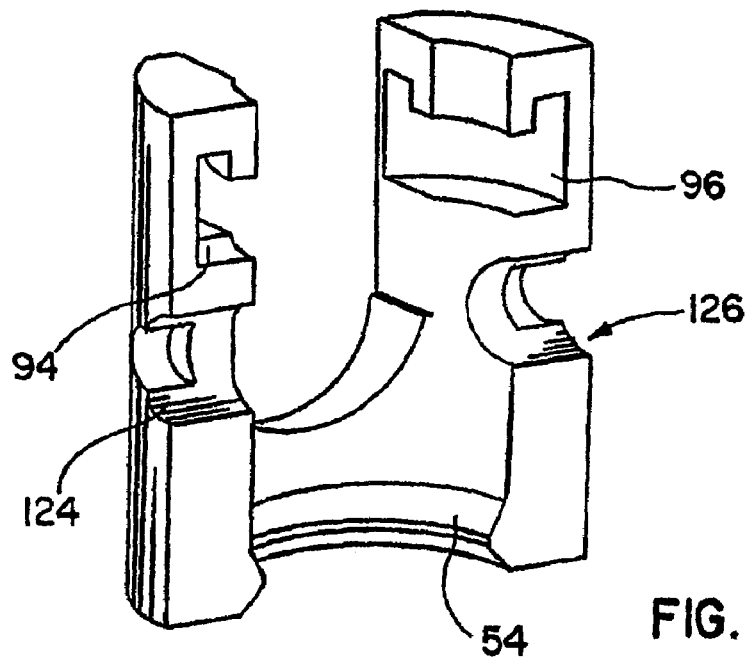
Figure 13:
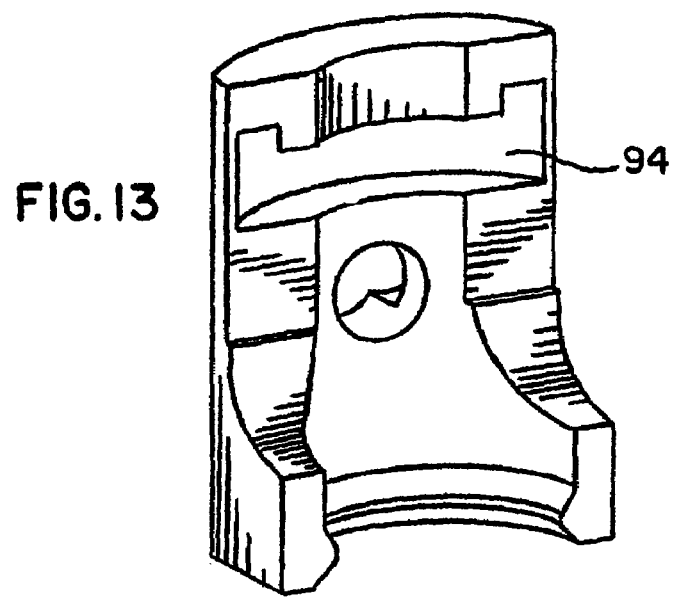
Figure 14:
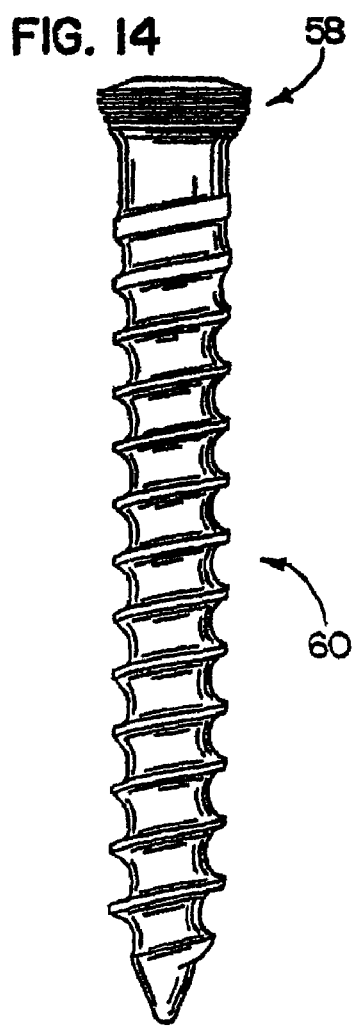
FIGS. 14 and 15 are elevational and sectional views, respectively, of the bone screw anchor member.

Similar to the cam lock member 18, the coupling member 20 also has a relatively small axial extent between top and bottom surfaces 38 and 40 thereof. As best seen in FIG. 11, the body 22 of the coupling member generally has a U-shaped or yoke configuration including opposing upstanding walls 42 and 44 spaced from each other by the rod openings 24 and 26 which can have an elongate configuration and be open to the top 38 of the coupling member body 22. Since the cam lock member 18 need not be advanced down along the walls 42 and 44 in the direction 21, the size in this direction can be minimized. By way of example and not limitation, the length or distance that the walls 42 and 44 extend between the top 38 and bottom 40 of the coupling member body 22 can be approximately 13.47 millimeters. The cam lock member 18 has a profile along axis 21 between the top 32 and the lowest most point of the contoured bottom cam surface 34 of approximately 5.08 mm.

Figure 7:
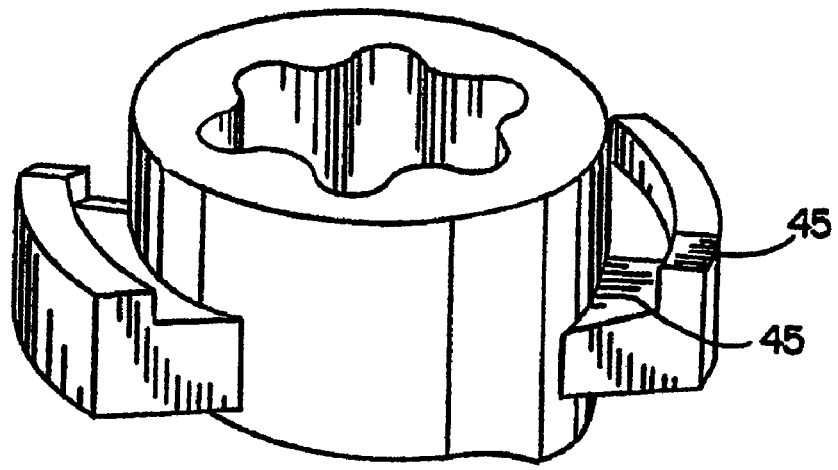
FIGS. 7-10 are various views of the cam lock member.

As shown, the annular body 30 of cam lock member 18 is sized to fit in internal space 46 of the coupling member 20 between the arcuate walls 42 and 44 thereof. The walls 42 and 44 are free of threading or cam surfaces that cooperate with the cam lock member 18 for shifting it to a locked position. More particularly, the inner surface 48 of the coupling member 20 including arcuate surface portions 42a and 44a on the respective coupling member walls 42 and 44 are sized to closely receive the outer surface 31 of the cam lock member annular body 30 therebetween. These surface portions 42a and 44a are each free of threading or cam surfaces and thus only serve as guide surfaces for the cam lock member body 30 as it is turned about axis 21. Since the walls 42 and 44 do not need to be threaded or provided with recessed cam surfaces or the like, the size of the coupling device 14 can be kept to a minimum in the widthwise direction along the axis 16a of the spinal rod 16 as well. By way of example and not limitation, the diametrical width of the coupling device along spinal rod axis 16a can be approximately 10.03 millimeters. As can be seen in FIG. 7, guides 45 may be provided. The guides 45 are provided to initially pilot the cam lock member 18 into engagement with the walls 42 and 44.

Referring next to FIGS. 3 and 4, the illustrated spinal fixation system 10 has a polyaxial bone screw 12 whose orientation can be changed such that its longitudinal axis 12a extends transverse to the axis 21 of the coupling device 14 or is substantially aligned therewith. To this end, the coupling device 18, and specifically the coupling member 20 thereof is provided with a bottom throughbore 50 that extends through bottom wall 52 of the coupling member 20. The bottom wall 52 includes an inner surface portion 54 that tapers or curves inwardly from the surface portions 42a and 44a toward the center axis 21. The diameter across the inner surface portion 54 at its lowermost end 56 is sized to be smaller than an enlarged head 58 of the bone anchor screw 12. In addition, the diameter at 56 is sufficiently large to allow the threaded shank 60 depending from the screw head 58 to be advanced therethrough. In this manner, the inner surface portion 54 serves as a seating surface for the screw head 58. As an alternative, the diameter 56 is threaded with a thread oversized relative to the shank 60, thereby allowing the screw shank 60 to be loosely threaded through. In this instance, the diameter 56 is sized as to hold the shank 60 from passing easily through so that the screw 12 and coupling member may be handled by a surgeon as a single component during the operation. In addition, the oversized threads allow the screw to be polyaxial in its orientation. As a further alternative, the screw 12 may be passed through the diameter 56, and a c-ring or radial spring may be attached to the screw 12 immediately adjacent to the coupling member 20, thereby holding the two together and allowing the surgeon to utilize them as a single component during the operation.

The throughbore 50 extends centrally through the inner surface portion 54 and includes an enlarged diameter lower portion 62 formed by tapered or curved surface portion 64 on the bottom wall 52 of the coupling member 20. The tapered surface portion 64 extends from the smallest diameter of the bore 50 at 56 tapering outwardly relative to the center axis 21 of the coupling member 20 to the bottom surface 40 thereof.

The enlarged bore portion 62 allows the screw 12 to swivel or pivot to a variety of different orientations thereof relative to the coupling device 14. For example, in the illustrated form, the enlarged bore portion 62 allows the screw shank to pivot by 20 degrees on either side of the coupling device axis 21. As the screw 12 is pivoted, the outer arcuate surface 66 of the screw head 58 rides or shifts on the tapered seat surface 54 in the coupling member 20. Once the orientation of the coupling device 14 relative to the bone screw 12 fastened into a vertebral bone is determined with the spinal rod 16 extending through the coupling member 20 and up along the spinal column, the cam lock member 18 is then turned to its locked position. In the locked position, the cam lock member 18 anchors the rod 16 to the spinal column so it is fixed relative to the bone screw 12 fastened into a vertebral bone with the bone screw head 58 clamped against the seat 54 therefor in the coupling member 20 thereby fixing coupling device 14 against shifting relative to the bone screw 12. The outer screw head surface 66 can be configured with concentric friction enhancing ridges or helical threads 67 to enhance the locking action between the screw head 58 and the seat 54.

Continuing reference to FIGS. 3 and 4, it can be seen that in the preferred and illustrated polyaxial spinal fixation system 10, the spinal rod 16 is pushed downwardly for being clamped against a small anvil insert 68. It should be noted that the previously described low profile coupling device 14 could be employed in spinal fixation systems that are not polyaxial and/or which do not employ an insert as described hereinafter.

Similarly, the present insert 68 could be advantageously employed in systems that employ threads or cams in the coupling members thereof.

The insert 68 has an upper anvil surface 70 that engages against the underside of the spinal rod surface 28 to maintain enhanced contact therewith over the curved surfaces of bone screw heads used in prior systems. The insert 68 has an upper surface 70 that may be substantially flat, may have radially oriented concave paths or valleys so that the insert 68 rotates to the closest path to meet with the spinal rod surface 28, or may have a cup or peripheral ridge that deforms when compressed by the spinal rod 12 to form a path without deforming the spinal rod. Accordingly, the insert 68 provides at least a line of contact with the curved rod surface 28, whereas prior systems engaging spinal rods with their curved fastener heads have a point contact with the spinal rod when clamped thereagainst which can more easily damage the rod 16.

Figure 5:
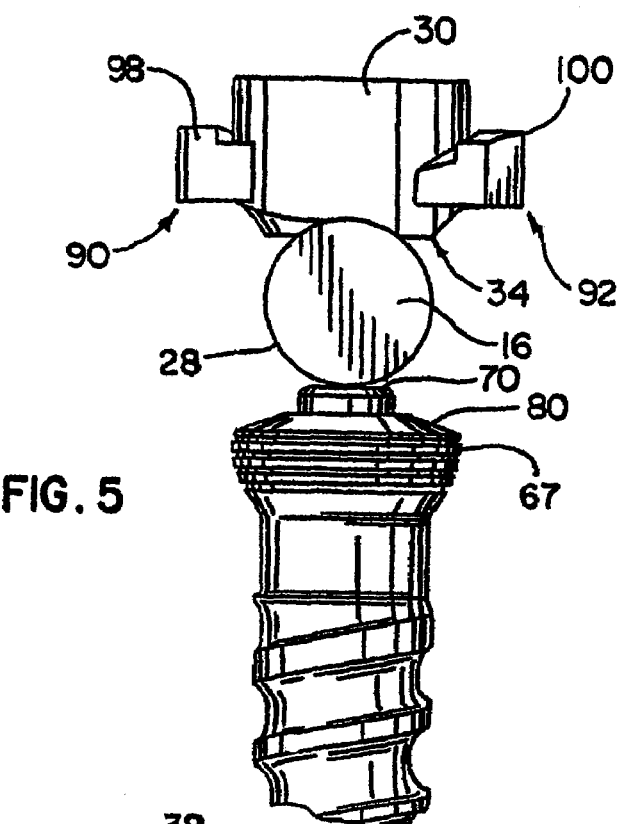
FIG. 5 is an elevational view similar to FIG. 2 with the coupling member removed to show the radial flanges on the cam lock member and a bottom cam surface thereof.

The present insert 68 is also provided with a very low profile to minimize the space it takes up in the coupling member 20. More particularly, the bone screw anchor 12 has an upper concave recess 72 formed in the screw head 58 thereof to form a cup-shaped wall 73 of the screw head 58 having an upwardly opening cavity 74 in which insert 68 is received. The insert 68 has an arcuate bottom surface 76 having a curvature similar to that of the concave surface 72 so that it can shift or slide thereon as the polyaxial screw 12 is moved to various orientations thereof relative to the coupling device 14. The insert 68 is sized such that the distance between the lowermost point of the bottom surface 76 and the top flat surface 70 is slightly larger than the depth of the cavity 74. In this manner, the flat surface 70 projects only slightly above the proximal end 78 of the screw 12 at the top surface 80 of the screw head wall 73 extending about the cavity 74, as can be best seen in FIG. 5. Accordingly, the insert 68 only nominally increases the height of the screw head 58 in the internal space 46 of the coupling member allowing the coupling device 14 to maintain its low profile character, as previously described. By way of example, the distance between the bottom 40 of the coupling member 20 and the spinal rod axis 16a with the rod 16 clamped against the insert 68 can be approximately 6.34 millimeters. It is preferred that the insert 68 has a greater elastic deformation than the coupling member 20 or the spinal rod 16 so that it has a greater spring-like property. Accordingly, the material of the insert 68 preferably has a lower Young's Modulus than the coupling member 20 and spinal rod, thereby reducing the criticality of the dimensional tolerances. Alternatively, a material, such as cobalt chrome, may be used for the insert 68 that is harder than the rod to increase the clamping force therebetween.

In the preferred and illustrated form, the small, low profile insert 68 has an enlarged lower portion 82 including the arcuate bottom surface 76 thereon with an upper portion 84 projecting centrally upward from the enlarged lower portion 82 and having the top surface 70 thereon. Accordingly, the top surface 70 is narrower in the directions orthogonal to the axis 21 than the bottom surface 76 so that a shoulder surface 86 is formed between the insert portions 82 and 84. The above-described structure for the low profile insert 68 provides it with an inverted mushroom-like configuration with the enlarged head portion 82 riding on the concave recess surface 72 in the screw head 58.

To keep the insert 68 in the cavity 74 formed in the screw head 58, a retainer such as in the form of staked portions 88 of the screw head wall 73 are provided. These staked portions 88 extend radially inward at the proximal end 78 of the screw 12 so as to be in interference with the shoulder surface 86 on the insert 68 for keeping it retained in the cavity 74, and in a substantially upright position while providing for a small amount of rotation therein as shown in FIGS. 3-6. It should be noted that the term rotation is meant to include any pivoting of the insert within the screw head 58. As can be seen, the insert 68 is not fixed with respect to the coupling member 20, instead being retained in the screw head with the staked portions 88. This allows the insert 68 to have a slight mobility, or play, and allows the insert 68 to shift independently of the screw 12 and the rod surface 28. Accordingly, the insert 68 may follow the rod surface 28 and seat itself between the rod surface 28 and the screw head 58 for a self-aligning capability.

Figure 6:
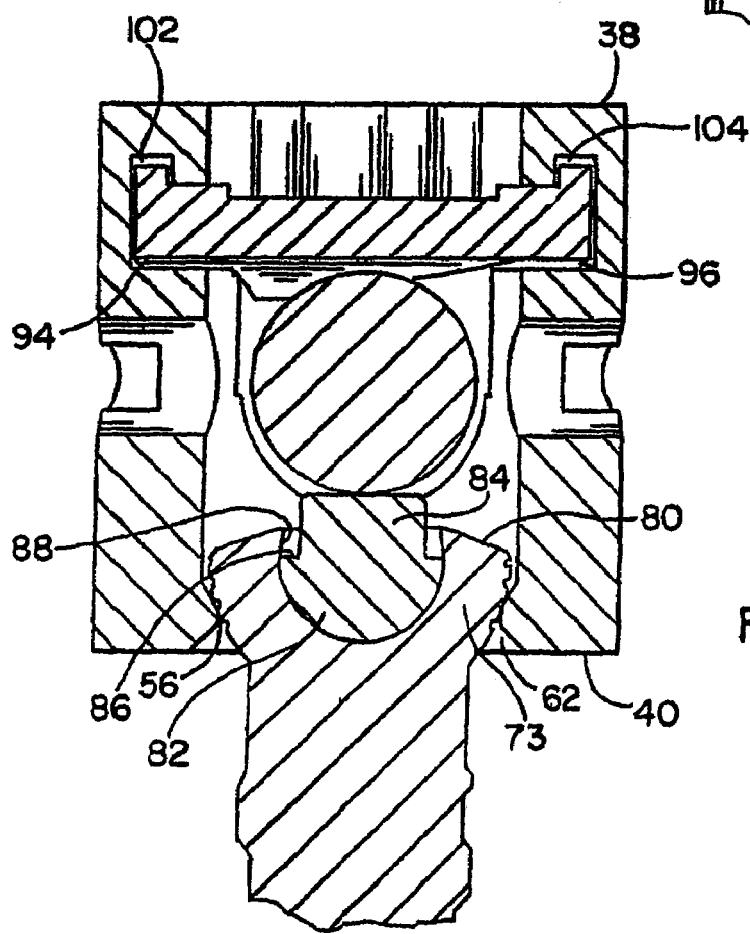
FIG. 6 is a cross-sectional view of the spinal fixation system showing the recesses formed in the coupling member configured to receive the radial flanges on the cam lock member.

As previously mentioned, the cam lock member 18 does not translate along the coupling member 20 when it is turned to its locked position. In order to keep the cam lock member 18 fixed against movement in the direction along axis 21, it is provided with radial flanges 90 and 92 extending radially outwardly from the annular body 30 at diametrically opposite positions thereon. The flanges 90 and 92 are received in correspondingly configured recesses 94 and 96 formed in the coupling member walls 42 and 44, as can be seen in FIG. 6. The recesses 94 and 96 have an arcuate configuration extending about axis 21 as do the radial flanges 90 and 92 for fitting therein and allowing turning of the cam lock member 18 between unlocked and locked positions thereof. The flanges 90 and 92 are received in the recesses 94 and 96 when the cam lock member 18 is turned toward its locked position. With the cam surface 34 camming on the rod surface 28, the flanges 90 and 92 in the closely conforming recesses 94 and 96 prevent the cam lock member 18 from shifting upwardly away from the spinal rod 16 and instead forces the spinal rod 16 down into clamping engagement with the insert 68 which, in turn, causes the screw head 58 and specifically outer head surface 66 to be clamped against the seat surface 54 in the coupling member 20 thus fixing the coupling device 14 relative to the bone screw 12 and anchoring the spinal rod 16 to the spinal column.

The downwardly directed clamping forces exerted by the cam lock member 18 between the screw head 58 and the bottom wall 52 of the coupling member 20 and in particular between the respective engaging surfaces 66 and 54 thereof can cause the coupling member walls 42 and 44 to spread apart. Accordingly, the flanges 90 and 92 are also provided with distal portions 98 and 100, respectively, that extend along axis 21.

In this instance, the distal portions 98 and 100 are shown as being upturned from the distal ends of the radial flanges 90 and 92 although they could likewise be configured so that they extend downwardly in the direction along axis 21. The recesses 94 and 96 also include portions 102 and 104, respectively, that extend in an upward direction along the axis 21 in the coupler member walls 42 and 44 for receiving the upturned distal portions 98 and 100 on the respective radial flanges 90 and 92. With the flange portions 98 and 100 received in the recess portions 102 and 104, any spreading action of the walls 42 and 44 during the locking operation with turning of the cam lock member 18 is resisted.

As previously mentioned, the cam lock member has a contoured bottom cam surface 34 that cams on the curved cam surface 28 of the spinal rod 16. The cam surface 34 is best seen in FIGS. 8 and 10. In the illustrated and preferred form, the cam surface 34 is contoured to provide three distinct regions defined in relation to their action on the spinal rod 16. A first concave region 106 is provided to substantially mate with the rod surface 28 in the unlocked position. Concave surface region 106 extends across the bottom 34 of the cam lock member body 30 and can be aligned with the radial flanges 90 and 92. Accordingly, the radial flanges 90 and 92 will be disposed slightly above the bottom 34 of the cam lock member body 30 to accommodate the spinal rod curved surface 28 extending therebelow with the cam lock member 18 in the unlocked position thereof. In this position, the flanges 90 and 92 are not received or fully received in the recesses 94 and 96 therefor.

Diametrically opposite sections 106a and 106b of the concave surface region 106 are provided so that rotation of the cam lock member 18 in the unlocked position does not cause a camming action to occur with only a slight initial turning action thereof. With the spinal rod surface 106 aligned with the surface portions 106a and 106b, the spinal rod 16 is still loosely received under the cam lock member 18 and is not cammed thereby. Beneficially, the spinal rod 16 is captured under the cam lock member 18 so as to provide the surgeon with greater freedom of manipulation before finally locking the cam lock member 18. With continued turning of the cam lock member 18, the camming action begins at ramp regions 108 and 110 that are diametrically opposite to each other on the cap bottom surface 34 and project downwardly from the adjacent surface sections 106a, 106b along direction 21. The ramp regions 108 and 110 are configured so that the rod 16 is progressively pushed downward in the direction 21 as the cam lock member 18 is turned about the turning axis 21 toward the locked position. Accordingly, in the unlocked position these ramp surface regions 108 and 110 on the bottom cam surface 34 extend down along either side of the spinal rod 16 so as to advantageously take up the space on either side thereof thus serving to keep the space occupied by the cam lock member 18 in the coupling member 20 to a minimum for providing the overall coupling device 14 with a low profile.

Continued turning of the cam lock member 18 toward the locked position causes the rod surface 28 to be engaged against diametrically opposite generally flat surface regions 112 and 114 adjacent to the ramp surface regions 108 and 110, respectively. In an alternative form, the surface regions 112 and 114 may be a valley shape providing a depression such that the rod 12 is received into the depression. The surface regions 112 and 114 are not inclined relative to the axis 21 like the preceding ramp surfaces 108 and are the lowest point of engagement of the cam surface 34 with the rod surface 28. With the cam lock member 18 turned so that the rod surface 28 is only engaged by the surface regions 112 and 114, the cam lock member 18 is in its fully locked position with the cam lock member flanges 90 and 92 fully received in the corresponding yoke wall recesses 94 and 96 therefor, as shown in FIGS. 1 and 6. Continued turning of the cam lock member in the same direction after the fully locked position has been reached is prevented by abutment surface regions 116 and 118 adjacent to the surface regions 112 and 114, respectively. These abutment surfaces 116 and 118 extend further downwardly in direction 21 from the surface regions 112 and 114.

Accordingly, the illustrated and preferred programmed cam surface 34 provides several stages for the camming and locking action on the spinal rod 16. As shown, the cam lock member 18 can be rotated by approximately 20 degrees from the unlocked position before the rod surface 28 reaches the ramp surfaces 108 and 110. At this point, the rod 16 is cammed downwardly and the cam lock member can be turned for another 60 degrees before the rod surface 28 reaches the flat locking surfaces 112 and 114. The cam lock member 18 can then be turned by another 20 degrees before the rod surface 28 abuts against the stop surfaces 116 and 118 and the cam lock member 18 is in its fully locked position. Thus, there is approximately 100 degrees of rotation of the cam lock member 18 that is required from the fully unlocked position to the fully locked position with 20 degrees of play provided before the camming action begins and the camming of the rod 16 occurring over the final 80 degrees of rotation to the fully locked position.

Turning to more of the details, as previously mentioned, the cap cam lock member 18 includes drive surface portion 36 recessed in the top surface 32. As best seen in FIG. 2, the drive surface portion 36 can be formed with a plurality of lobes extending radially outward from the center axis 21 for receiving a similarly lobed drive tool. The lobe drive surface portions 36 provide an increased area for surface contact and torque transmission between the drive tool and the cam lock member 18.

Figure 15:
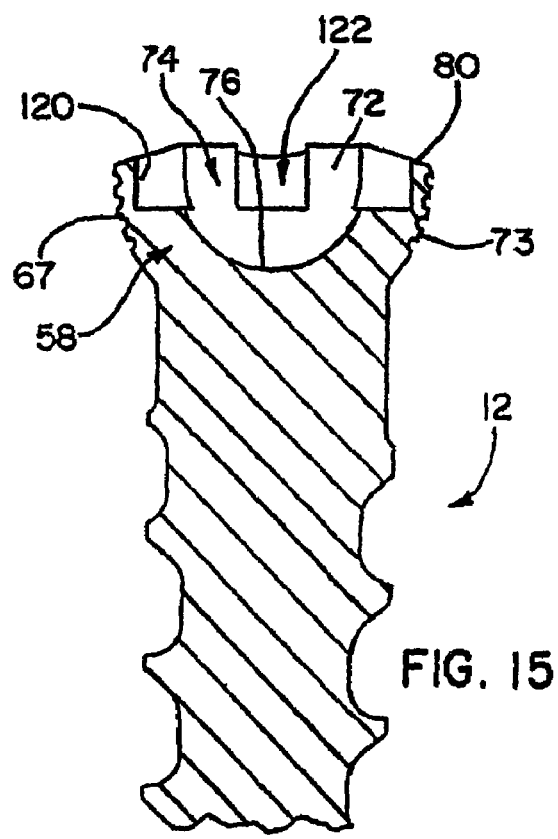

For the bone screw 12, the screw head 58 is provided with peripheral driving surfaces 120 and recessed notches 122 formed in the proximal end 78 of the screw head and recessed or notched into the top surface 80 thereof, as can be seen in FIG. 15. In this manner, a driving tool having peripheral prongs for fitting in the notches 122 can be utilized while the anvil insert 68 is in the screw head cavity 74 and slightly projecting out therefrom, as previously described.

Referring to FIGS. 1 and 11-13, it can be seen that the yoke coupler walls 42 and 44 are provided with a key slot 124 and 126, respectively, with the slots 124 and 126 having enlarged central throughbore 128 and 130 extending through the walls 42 and 44.

The slots enable the coupling device 14 to be held as by arms on a device used to insert the spinal rod 16 into the coupling member 20, e.g., a rod persuader. The arms can have engaging ends that locate in the slots 124 and 126 and extend into the throughbores 128 and 130.

Figure 19:
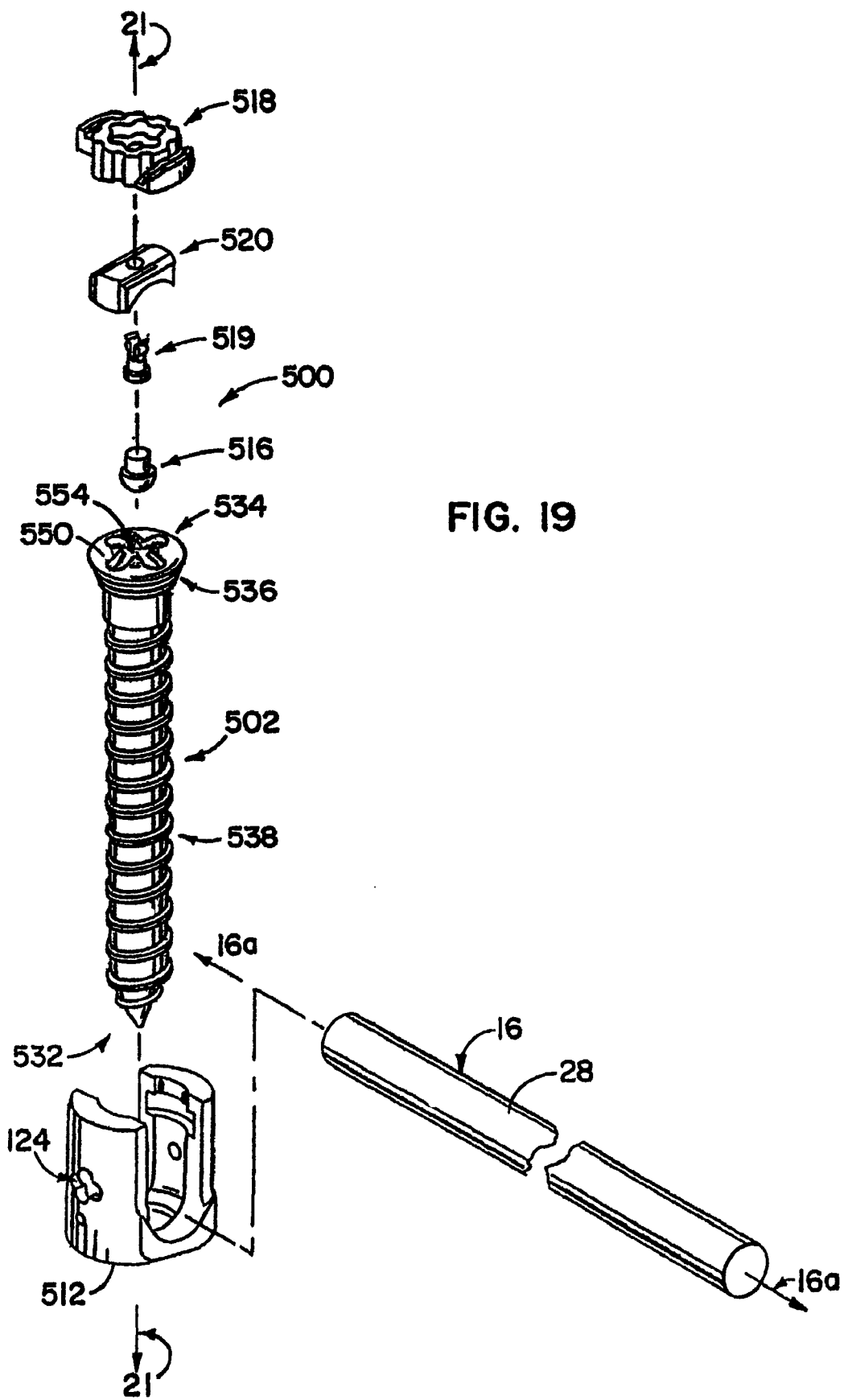
FIG. 19 is an exploded perspective view of another form of the spinal fixation system in accordance with the present invention showing a bone screw and a coupling device including a coupling member, a cam lock member, a spring clip connector member, a clamping member, and an insert for securing a spinal rod relative to the bone screw.
Figure 25:
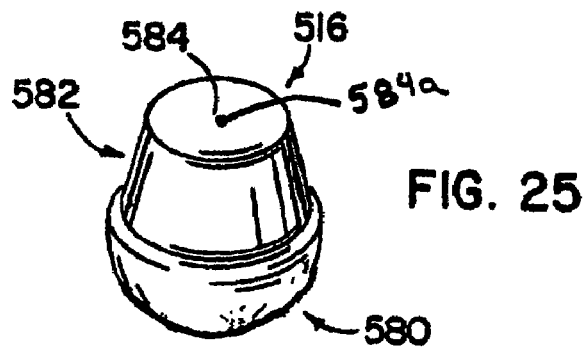
FIG. 25 is a perspective view of the insert showing a flat upper anvil surface thereof.

Referring now to FIGS. 19-44, a low profile spinal fixation system 500 for securing a spinal rod 16 in accordance with another form of the present invention is depicted. As can be seen in FIGS. 19 and 20, the system 500 includes a bone anchor member such as screw 502 and a coupling device 504 for securing the spinal rod 16 relative to the bone screw 502. The coupling device includes a coupling member in the form of a unitary yoke 512, an insert in the form of anvil 516, a cam lock member in the form of cap 518, a connector member in the form of a spring clip 519, and a clamping member in the form of a saddle 520. The fixation system 500 is similar to the embodiment of FIGS. 1-18 in that the cap 518 and yoke 512 are provided with a very low profile in the direction indicated by yoke axis line 21 extending transverse and specifically orthogonally to the axis 16a of the spinal rod 16 fixed relative to the bone screw 502 by the coupling device 504, as best seen in FIG. 20.

The screw 502 is directed through the yoke 512 and attaches the yoke 512 to a bone or bone fragment. The screw 502 has a head 536 with a recess 554, and the recess 554 receives the anvil 516. The spinal rod 16 is received within an internal space or channel 601 in the yoke 512 and is seated on top of the anvil 516. The screw 502 is preferably a polyaxial screw, and the anvil 516 is permitted to move within the head 536 of the screw 502. Accordingly, prior to the system 500 being secured, the screw 502 may move relative to the yoke 512 so that the yoke 512 and screw 502 may be selectively positioned to assume different orientations relative to each other so that their respective axes 21 and 544 are not necessarily aligned with each other, and the anvil 516 may move and pivot or rotate relative to the screw 502 so that the anvil 516 may be properly positioned by orienting itself with the outer surface 28 of the rod 16 similar to the previously described anvil 68.

The rod 16 is secured or locked within the yoke 512 with the cap 518 and saddle 520. As will be discussed below, rotation of the cap 518 has the dual function of securing the cap 518 within recesses 642 in the yoke 512 and of forcing the saddle 520 against the rod 16 to lock the rod 16 between the saddle 520 and the anvil 516. The saddle 520 and cap 518 are secured together in assembly by a distinct connector in the form of the dual-pronged, spring clip 519.

Figure 22:
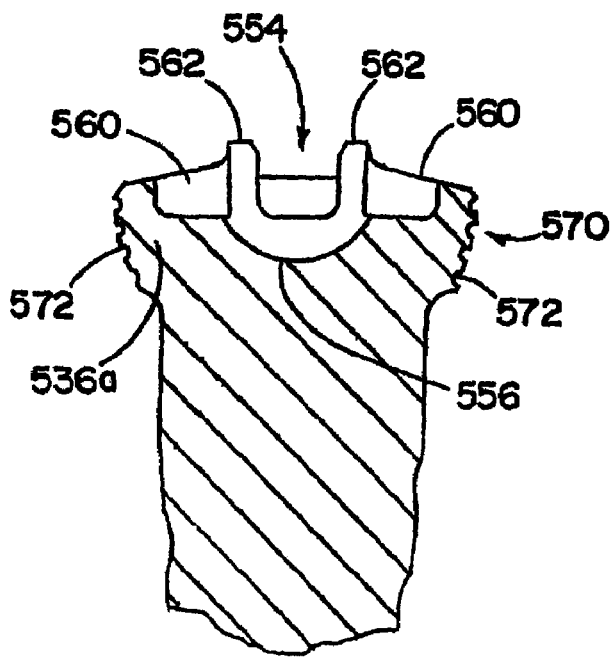
FIG. 22 is an enlarged cross-sectional view of a head of the bone screw of FIG. 21.
Figure 21:
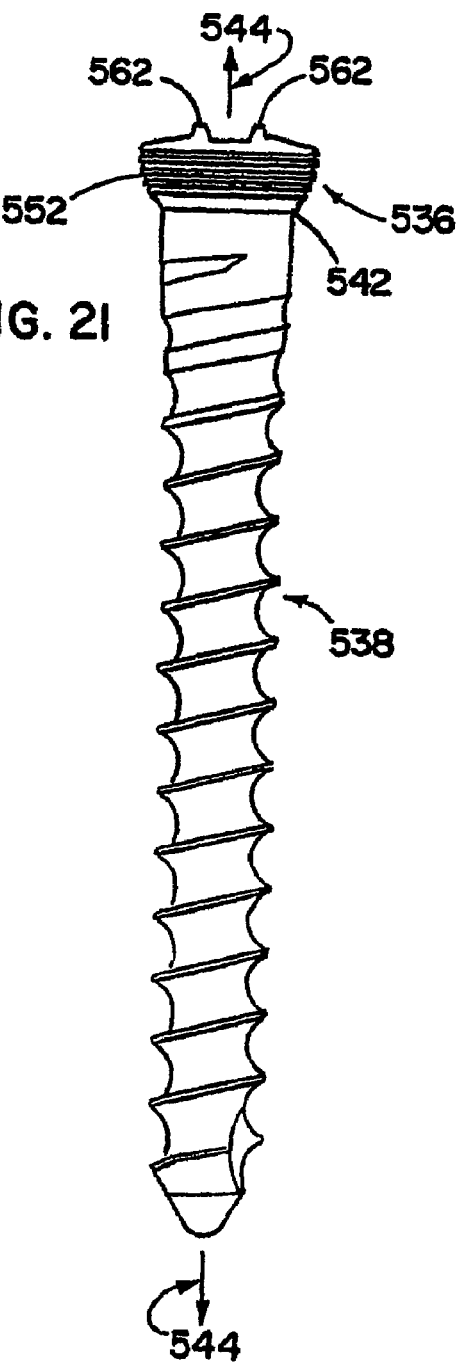
FIG. 21 is a side elevation view of the bone screw of FIG. 19.
Figure 23:
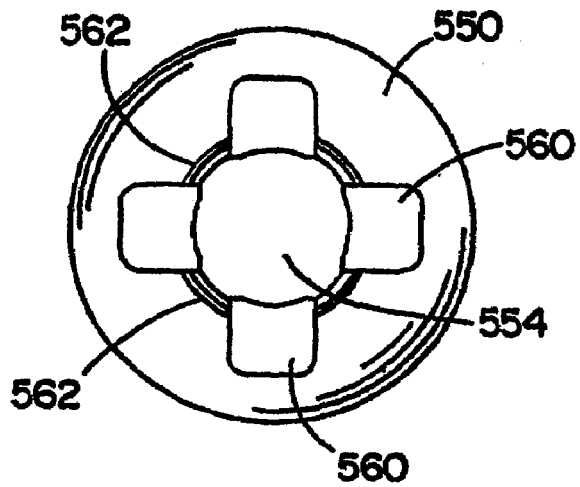
FIG. 23 is a plan view of the bone screw head showing a recess for the insert.
Figure 26:
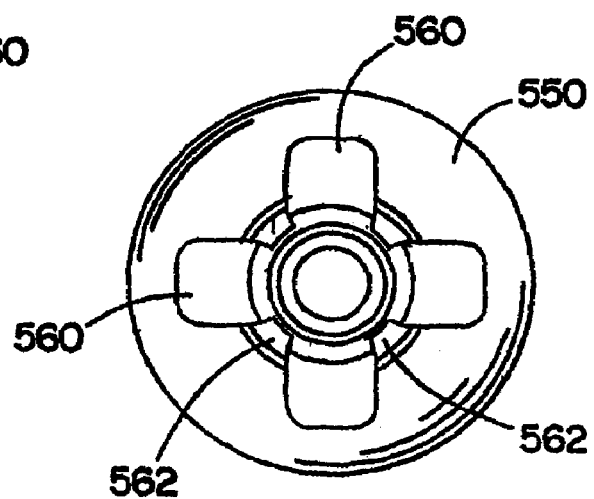
FIG. 26 is a plan view of the insert retained in the screw head recess.
Figure 27:
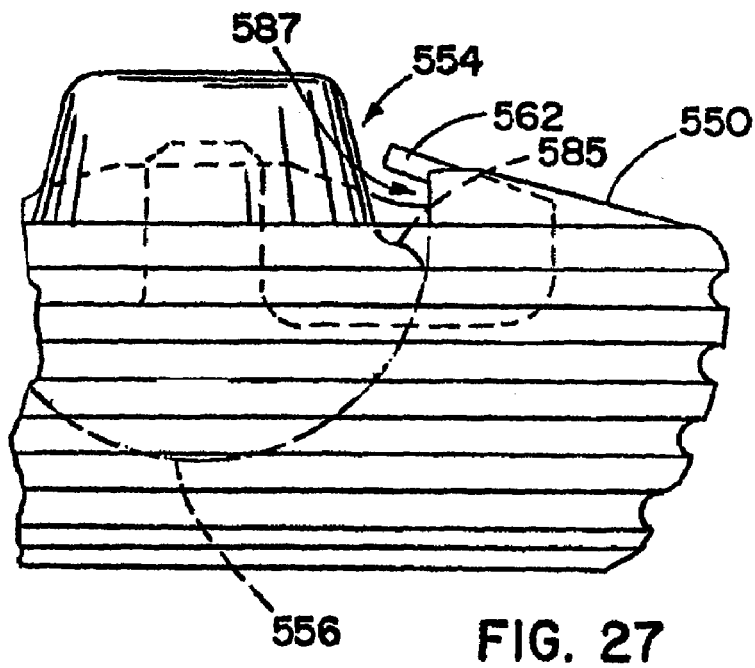
FIG. 27 is an enlarged cross-sectional view of the screw head and the insert showing one of the staked head portions that retain the insert in the head recess.

In FIGS. 21-22, the bone screw 502 is depicted. The bone screw 502 includes a tip 530 at a distal end 532, a proximal end 534 including a screw head 536, a shank 538 including external threads 540 for driving and securing the screw into a bone or bone fragment, and a neck 542 where the head 536 and the shank 538 meet. The screw 502 is driven by rotation around its central longitudinal axis 544. The tip 530 of the screw may be provided with a variety of configurations such as a self-tapping structure or self-drilling structure, as is known. As discussed, the screw 502 is preferably polyaxial, and the head 536 is diametrically larger than the shank 538 at the neck 542. The polyaxial features of the screw 502 allow the screw 502 to be secured to a bone in a desired orientation for proper fixation to the bone while allowing the yoke 512 to be oriented relative to the screw 502 in an orientation desired for seating a rod 16 therein.

The head 536 of the screw has an arcuate or slightly ramped top surface 550 which meets a peripheral outer surface 552 of the screw head 536. The peripheral outer surface 552 of the screw head 536 has a generally arcuate or spherical profile 570. The profile 570 is interrupted with a series of concentric ridges or circular grooves 572 cut therein. As discussed above, the screw 502 is polyaxial so that its orientation relative to the yoke 512 can be precisely positioned. When the coupling device 504 is secured to the screw 502, the grooves 572 grip or cut into the interior of the yoke 512 to immobilize the screw 502 in the desired position against the yoke 512. By way of example, the grooves 572 can be approximately 0.012 inches in width to provide sufficient gripping strength or purchase in the yoke 512.

The top surface 550 includes an upwardly opening recess 554 formed therein for receiving the anvil 516. As can be seen in FIGS. 24-27, the recess 554 has an arcuate or, preferably, spherical bottommost surface portion 556 sized and configured to allow the small anvil 516 to shift when seated in the recess 554. To this end, the anvil 516 has a bottom surface 558 supported on and slidable against the bottommost surface portion 556. Furthermore, the recess 554 has two pair of diametrically opposed notches 560, each pair perpendicularly oriented from the other pair, for receiving similarly configured prongs of a driver without interfering with the anvil 516 therein. The top surface 550 includes a retainer or staked portion in the form of short tabs 562 located at the opening to the recess 554 and between each notch 560. Prior to disposing the anvil 516 in the recess 554, the tabs 562 rise upwardly from the top surface 550 in the axial direction so that the tabs 562 do not hinder insertion of the anvil 516. Once the anvil 516 is located in the recess 554, the tabs 562 are deflected over to extend radially into interference with the anvil 516 while still allowing the anvil 516 to move within the recess 554 but be captured therein by the tabs 562. After assembly, heat or other treatment may be utilized to relieve residual stresses within the bent tabs 562.

The anvil 516 has a bottom portion 580 with a generally arcuate or spherical bottom surface 558 which rests against the bottommost portion 556 of the seat 554.

Accordingly, the anvil 516 may pivot or rotate within the recess seat 554. The anvil 516 further includes a seat portion 582 extending centrally upward from the anvil bottom portion 580 to a top surface 584 with a transverse shoulder surface 585 between the anvil portions 580 and 582. As seen best in FIG. 27, with the anvil 516 seated upright in the recess 554 there is a gap spacing 587 between the bent tabs 562 and the anvil transverse surface 585. This gap spacing 587, along with the narrower width of the anvil upper portion 582 extending generally upwardly in the recess 554, allows for the anvil 516 to toggle or pivot in the recess 554 with the anvil surface 558 sliding on the recess surface 556 until the surface 585 abuts against one or more of the tabs 562.

The seat portion 582 is preferably frusto-conical so that compression stresses thereon are distributed through to the bottom portion 580 while minimizing the possibility of damage to the outer edge 584a of the top surface 584. Like the previously described anvil 68, the anvil bottom portion 580 is enlarged relative to the upper portion 582 so that the seat portion 582 may move within the recess 554 and in the space 587 between the anvil shoulder surface 585 and the tabs 562.

When the rod 16 is inserted within the yoke 512, the side surface 28 of the rod 16 is advanced into contact with the anvil 516. If the bone screw 502 is deflected, angled or secured so that its central axis 544 is not coincident or aligned with the yoke central axis, the anvil 516 is initially deflected or tilted in a similar direction. As the rod 16 is secured and forced against the anvil 516, the anvil 516 pivotable in the recess 554 will shift to require the minimize distance between the rod 16 and the bottom surface portion 556 of the recess 554. As the anvil top surface 584 is flat while the bottom surface 558 is spherical, the shortest distance from the top surface 584 to the bottom surface 558 is through the geometric center 588 to the center 590a of the bottom surface 558.

As discussed herein, in order to have a low profile, it is preferred to minimize the height of the anvil 516 while remaining above the top surface 550 of the screw head 536.

The anvil top surface 584 is sized so that, when angled or deflected due to the angle or deflection of the bone screw 502, at least a portion of the top surface 584 is contacted by rod 16 being advanced towards the anvil 516 in the yoke 512. Accordingly, the anvil 516 is self-righting as the rod 16 contacting the anvil top surface 584 forces the anvil 516 to shift to align tangentially its minimum height, as discussed above, with the surface 28 of the rod 16.

Figure 24:
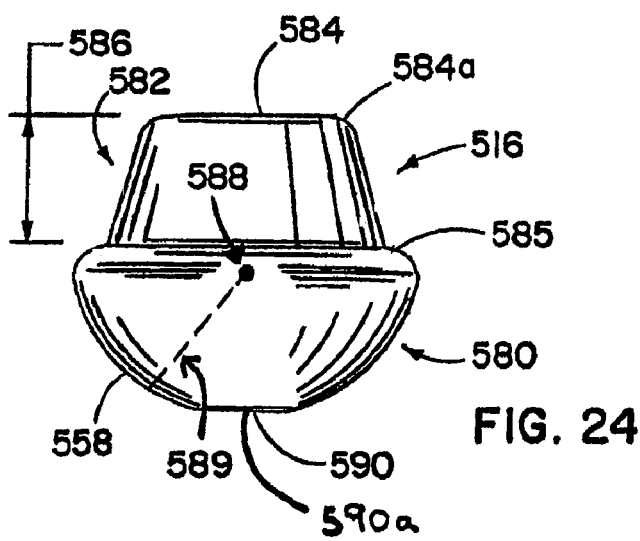
FIG. 24 is a side elevation view of the insert of FIG. 19 showing an enlarged arcuate lower portion and a narrower upper portion projecting upward from the lower portion.

The polyaxial screw 502 is inserted through the yoke 512 and secured to a bone, and the rod 16 rests against the top surface 584 of the anvil 516. As the orientation of the screw 502 relative to the yoke 516 may pivot, the anvil 516 may pivot within the recess 554 so that the top surface 584 remains tangential to the generally cylindrical outer surface 28 of the rod 16. Generally, the anvil 516 and screw head 536, and specifically the recess 554 thereof are sized relative to each other so that the anvil top surface 584 always extends slightly beyond the top of the cup-shaped head wall 536a at the head upper surface 550 even with the screw 502 pivoted to its maximum extent relative to the yoke 512, e.g., twenty degrees from axis 21. More specifically, as previously mentioned, the anvil bottom portion 580 can have its bottom surface 558 curved to have a generally spherical configuration with a radius 589, as shown in FIG. 24. As the bottom surface 558 pivots in the arcuate recess surface 556, the radius 589 extends from the general center of rotation 588 of the anvil 516. The anvil 516 is fashioned from a generally spherical component to have the shoulder surface 585 and the seat portion 582.

Accordingly, the height distance 586 from the center of rotation 588 to the anvil seat surface 584 is at least slightly less than the length of the radius 589. By way of example, the height distance 586 can be approximately 0.043 inches and the radius 589 can be approximately 0.0625 inches so that the distance is approximately 0.0195 inches less than the radius. If the height 586 of the anvil top surface 584 is increased significantly, the width of the anvil top surface 584 must be increased which would limit the polyaxial motion of the screw 502 as the anvil 516 would come into contact with the tabs 562 with a smaller degree of tilt or deflection. If the height 586 of the anvil top surface 584 is decreased significantly, the rod 16 would not be able to contact anvil top surface 584 without contacting the screw head 536 first, an event that becomes more acute at greater deflection angles.

Thus, the configuration of the anvil 516 and the recess 554 including the tabs 562 1 extending therein allows the anvil 516 to pivot to follow the position of the rod 16 and to promote self-righting of the anvil 516. In addition, the size of the anvil 516 between surfaces 584 and 558 including the height 586 is selected so that the top surface 584 is lower than a top surface of a completely spherical screw head would be to keep the profile of the anvil assembly including the screw head 536 and anvil 516 in the yoke 512 to a minimum. That is, if the screw head 536 were spherical, the height of the top of the screw head 536 would be higher than the top surface 584 of the anvil 516, which would increase the overall height of the system 500. When the coupling device 504 is in its locked condition, the top surface 584 of the anvil 516 may slightly deform, thereby forming a depression which is tightly engaged with and conforming to the outer surface 28 of the rod. By deforming, the anvil 516 and rod 16 form a substantially flush mating surface contact, as opposed to a line contact. The bottom surface 558 of the anvil 516 includes a small flat 590 which assists in minimizing friction between the anvil bottom surface 558 and the seat 554.

As has been stated, the screw 502 is inserted through the yoke 512. As can be seen in FIGS. 28-32, the yoke 512 has an enlarged base portion 600 and a shape with a generally cylindrical outer surface 602 formed by a pair of opposed side wall portions 604, 606 extending from the enlarged base 600 and defining a channel 601 for receiving a rod 16 therebetween. The channel 601 may have a liner made of, for instance, a polymer such as PEEK, for promoting low-friction contact between the rod 16 and the channel 601. A recess 608 including the channel 601 is formed between the walls 604, 606 with vertical axis 21, and the recess 608 includes a throughbore 612 in the bottom or base 600 of the yoke 512 through which the screw 502 is inserted. The throughbore 612 may be constructed as the throughbore 50 of the coupling member 20, discussed above, and may include a polymer liner, such as PEEK, for promoting low-friction polyaxial movement of the screw 502 therein.

In similar fashion to that depicted in FIGS. 1 and 11-13, the outer surfaces 602 of the yoke walls 604, 606 are provided with a key slot 124 and 126, respectively, with the slots 124 and 126 having enlarged central throughbore 128 and 130 extending through the walls 604, 606. The slots enable the coupling device 514 to be held as by arms on a device used to insert the spinal rod 16 into the yoke 512, e.g., a rod persuader. The arms can have engaging ends that locate in the slots 124 and 126 and extend into the throughbores 128 and 130.

The outer surface 602 of the yoke 512 also includes blind apertures or holes 650.

Figure 32:
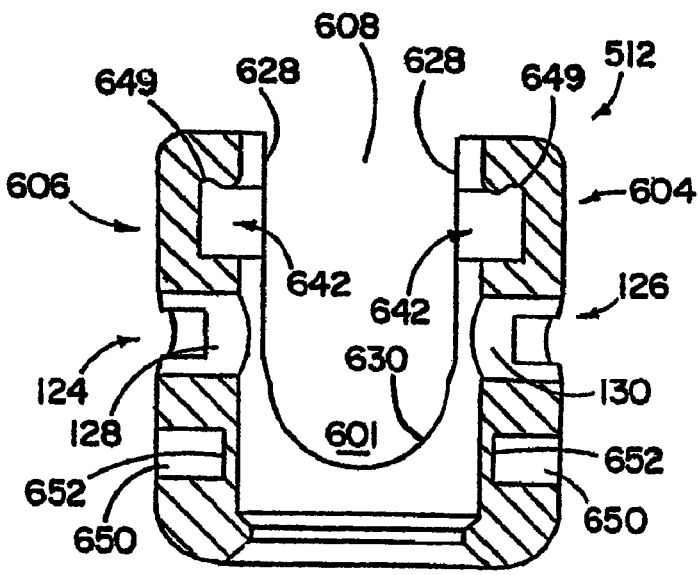
FIG. 32 is a cross-sectional view of the coupling member showing blind apertures toward the lower ends of the sidewalls.

As can be seen best in FIG. 32, the blind hole 650 does not extend into the interior recess 608, instead terminating at a thin wall portion 652 of the yoke 512. Once the screw 502 and its secured anvil 516 have been inserted through the throughbore 612, the thin wall portion 652 adjacent each blind hole 650 is deformed into the recess 608 so that the screw 502 and anvil 516 subassembly cannot be pulled back out of the yoke 512 and thus stays in assembly therewith. With the screw 502 retained in the yoke 512, the surgeon need only handle the screw 502, yoke 512, and anvil 516 as a single item or assembly.

Figure 31:
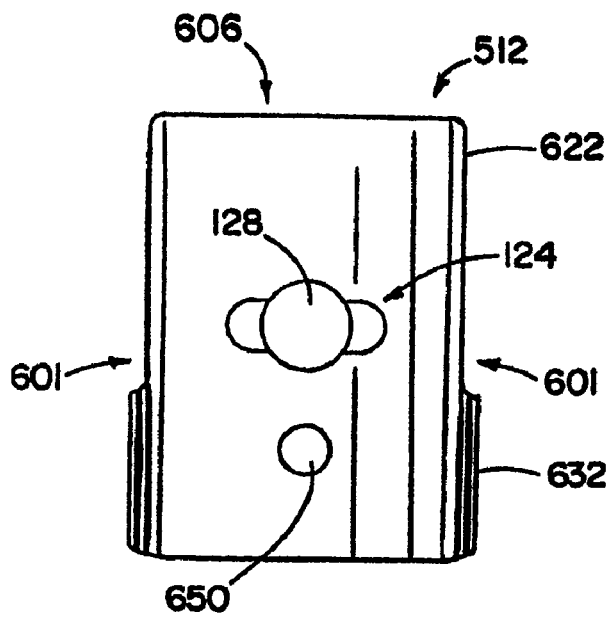
FIG. 31 is a side view of the coupling member rotated ninety degrees from the FIG. 30 view showing an enlarged width lower portion of one of the sidewalls at the base of the coupling member.
Figure 28:
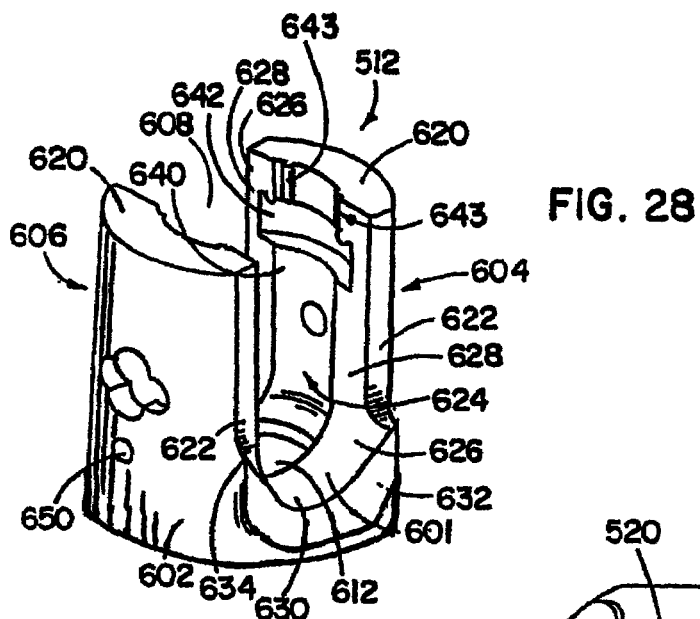
FIG. 28 is a perspective view of the coupling member of FIG. 19 including a pair of integral spaced sidewall portions.

In the preferred illustrated form, the yoke 512 has a high strength unitary construction as described below. Each integral sidewall portion 604, 606 has a top surface 620, end surfaces 622, and inner surfaces 624. The inner surface 624 of each wall 604, 606 is generally a mirror of the surface on the opposed wall. The walls 604, 606 cooperate with each other to form two U-shaped interior surfaces 626, each with a pair of leg portions 628 that are vertically opposed in a region from the top surface 620 extending downward. Each pair of leg portions 628 meets a generally semi-circular portion 630 interconnecting the leg portions 628. To the outside of the surfaces 626, the cylindrical outer surface 602 of the yoke 512 is truncated to form the end surfaces 622 of the walls 604, 606, and is truncated to form end surfaces 632 on the base 600. The truncation of the ends of the yoke 512 reduces the overall size of the yoke 512 in a widthwise direction transverse to the axial direction 21. Referring to FIGS. 28 and 31, as the base 600 has a greater dimension between its end surfaces 632 than the walls 604, 606 have between their end surfaces 622, there is a shoulder 634 formed between the end surfaces 632 and the end surfaces 622. The enlargement of the base portion 600 at the lower end portions of the walls 604 and 606 provides increased strength to the yoke 512 in the area of highest stress concentration where the rod 16 is clamped down on the curved surface portions 630 of the yoke 512 toward the bottom end thereof. The cut away of the yoke 512 along the side wall portions 604 and 606 extending up from the base portion 600 keeps the width of the yoke 512 for a majority of its axial length to a minimum, as previously described.

Figure 29:
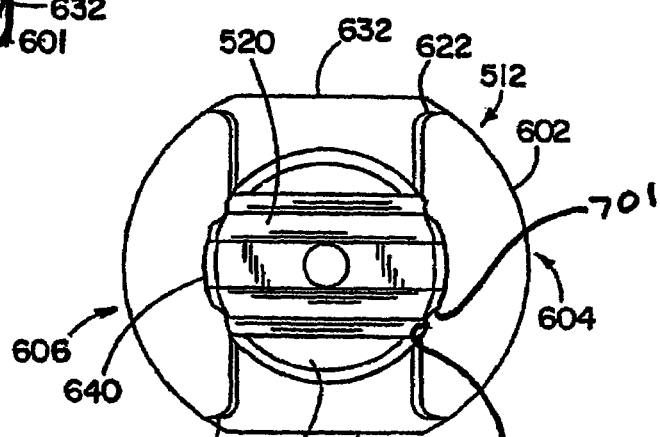
FIG. 29 is a plan view of the coupling member showing a bottom throughbore through which the bone screw extends, and a saddle located therewithin.
Figure 30:
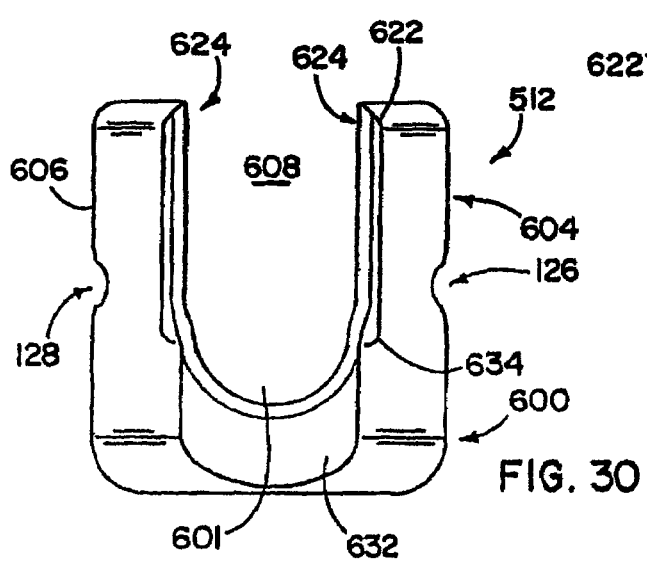
FIG. 30 is a side view of the coupling member showing the spacing between the sidewalls.

The inner surfaces 624 of the walls 604, 606 each include a surface 640 having a generally cylindrical configuration extending between the U-shaped interior surfaces 626. The cylindrical surfaces 640 and interior surfaces 626 define interior recesses 642 extending circumferentially in the sides with a constant cross-section. Guides 643 in the form of small projections or nubs are located on the interior surface 626, as depicted in FIG. 28, above the recesses 642. When the saddle 520 is inserted into the yoke 512, as seen in FIG. 29, the guides 643 assist in proper positioning of the saddle therein, as will be discussed below. In addition, the guides 643 serve as detents to provide distinct rotary positions for the cap 518 as it is turned. Similar to the cam lock member 18 described above, the cap 518 has a generally cylindrical body portion 644 with an outer surface 645 including a number of recesses arranged thereon in the form of generally vertical, arcuate indentations 647 circumferentially spaced about the outer surface 645. The indentations 647 cooperate with the detents 643 to provide a tactile indication to a surgeon as to how far the cap 518 has been turned in the yoke 512 as the nub detents 643 snap into and out from the indentations 647. For instance, with the cap 518 in its locked position, the detents 643 and indentations 647 can be spaced so that a predetermined number of clicks are generated when the cap 518 is turned to its completely locked position, e.g., one hundred degrees from the unlocked position.

The recesses 642 extend generally horizontally for receiving the cap 518 and, more specifically, a pair of radial flanges 656 of the cap 518 that fit into the correspondingly configured recesses 642 of the yoke 512 in a manner similar to previously described flanges 90 and 92 and corresponding recesses 94 and 96. The radial flanges 656 and recesses 642 keep the cap 518 from shifting axially along the yoke 512 as it is turned so that the camming action generated between the cap 518 and saddle 520 only causes axial shifting of the saddle 520 toward and against the spinal rod 16. Each of the flanges 656 includes a flat ramp lead-in surface 657 that assists in guiding the flanges 656 as they are turned from the slots formed between the sidewall portions 604 and 606 with the cap 518 in its unlocked position to shift the flanges 656 to be inserted in their respective recesses 642. No camming action, however, occurs between the surfaces of the recesses 642 and the flanges 656 that shifts the lower surface 700 of the saddle 520 relative to the cap 518. As explained below, the camming action is solely generated between the bottom surface 704 of the cap 518 and the top surface 702 of the saddle 520.

The radial flanges 656 also include upturned portions 658 at their distal ends 659, and the recesses 642 also include corresponding portions 649 that extend in an upward, axial direction in the respective yoke walls 604, 606 for receiving the upturned flange portions 658 therein. With the flange portions 658 received in the corresponding recess portions 649, any spreading action of the yoke walls 604, 606 during the locking operation with the turning of the cap 518 is resisted.

As depicted in FIGS. 41-44, the cap 518 and the saddle 520 each define central openings 670, 672, respectively, through which the clip 519 extends. The cap opening 670 is segmented between a lower portion 670a and an upper portion 670b that steps open to a diameter larger than that of the lower portion 670a. An annular shoulder seating surface 674 is at the transition between the lower portion 670a and the upper portion 670b of the cap opening 670. The upper portion 670b also opens to a recessed bottom surface 671 in the drive socket of the cap member 518.

Referring to FIGS. 36 and 37, the clip 519 includes an annular base portion 680 and two resilient prongs or stems 680a, 680b projecting upward therefrom along clip axis 683 and spaced by an axially extending gap 682 therebetween. Each stem 680a, 680b terminates at their free ends with flanges 681a and 681b including an upwardly facing cam surface 684 that can be ramped or inclined relative to the clip axis 683, or have a curvature thereto. The cam surfaces 684 aid in insertion of the clip 519 through the openings 670 and 672, and a corresponding lower stop surface 688 is provided at the prong flanged ends 681a and 681b extending normal to clip axis 683 that substantially prevents unintentional removal of the clip 519 back through the openings 670, 672.

The central opening 672 of the saddle 520 also includes an upper portion 672a and a lower portion 672b. The lower portion 672b opens to a concave bottom 700 of the saddle 520 and has a larger diameter than the upper portion 672a so that there is an annular shoulder surface 672a extending therebetween. The enlarged lower portion 672b is sized such that the base portion 680 of the clip 519 is fit and held therein in interference with the surface 672c. Preferably, the diameter of the opening lower portion 672b is kept to a minimum to increase the surface contact area of the saddle surface 700 on the rod 16. The opening upper portion 672a can be sized to have a similar diameter as that of the smaller lower portion 670a of the cap opening 670.

To assemble the cap member 518 and saddle member 520 together, initially the spring clip member 519 is axially inserted in saddle opening 672 with prong free ends 681a and 681b first inserted in enlarged lower opening 672b. With continued axial insertion, the cam surfaces 684 engage and cam against shoulder surface 672c resiliently forcing the spring prongs 680a and 680b toward each other to take up the gap 682 therebetween. With the prongs 680a and 680b pushed together, the lateral outer edges 684a of the cam surfaces 684 are spaced by a distance slightly less than the diameter of the opening portions 670a and 672a. This allows the clip member 519 to continue to be inserted through the opening 672 including the smaller diameter opening upper portion 672a. Depending on the distance across the undeformed prong upper edges 684a relative to the diameter of opening lower portion 672b, there may also be camming against the saddle surface 700 with some attendant prong deformation to enable the clip prongs 680a and 680b to fit into opening lower portion 672b. Once the prong ends 681a and 681b and specifically the prong surfaces 688 thereat clear the opening upper portion 672a, the clip prongs 680a and 680b return to their original undeformed state with surfaces 688 in confronting relation with upper surface 702 of the saddle 520 so that absent exerting a force to bring the prongs 680a and 680b together, the clip member 519 and saddle member 520 stay assembled together.

To complete the assembly process, the prong ends 681a and 681b are next axially inserted in the cap opening 670, and specifically smaller lower portion 670a thereof. Accordingly, the cam surfaces 684 cam against a lower surface 687 of the cap 518 about the central opening 670 therein which forces the resilient stems 680a, 680b together taking up the gap 682 therebetween to allow the clip prongs 680a and 680b to be inserted through the opening portion 670a. Once the clip cam surfaces 684 pass through the lower portion 670a of the cap opening 670, the stems 680a, 680b resiliently return back toward their non-flexed position. After the prong ends 681a and 681b exit the opening 670, the prongs 680a and 680b will return to their undeformed state, and the stop surfaces 688 will be facing the cap surface 671 and spaced therefrom so that there is play between the connected components, i.e., the cap 518, saddle 520, and clip 519, as shown in FIG. 42. Upon turning the cap 518 toward its locked position, the prong ends 681a and 681b re-enter the opening upper portion 670b as the saddle member 520 is driven toward the rod 16 shifting the spring clip member 519 axially therewith due to engagement of the surface 672c on the clip base 680 with the stop surfaces 688 brought into abutting engagement with the seating surface 674 to substantially prevent the clip 519 from being unintentionally pulled back through the openings 670, 672 during cap turning to its locked position.

Figure 41:
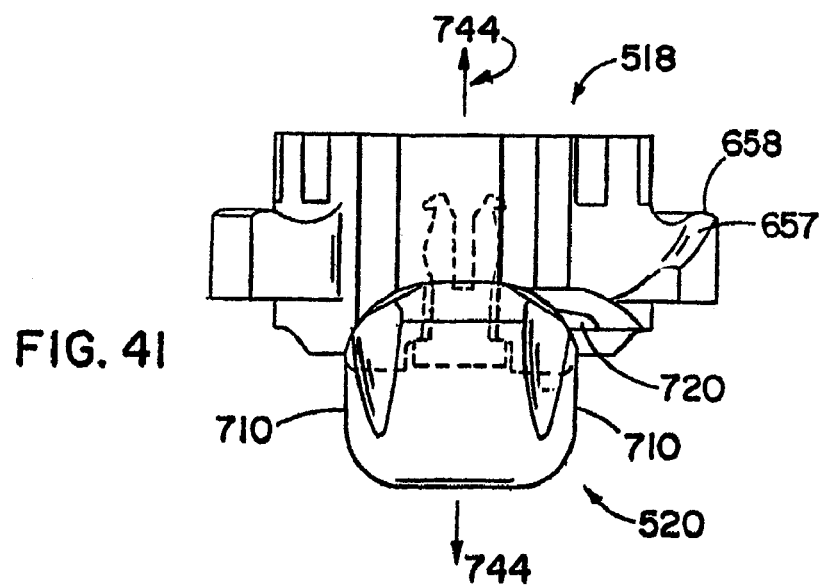
FIG. 41 is a side elevation view of the cam lock member, and the clamping member in a unlocked position relative to the spinal rod.

The stems 680a, 680b of the clip 519 further include an intermediate cam portion including a central, double-ramped cam surface 800. When initially prepared for implantation, the clip 519 holds the cap 518 and saddle 520 in a compact, assembled arrangement with the clip base 680 drawn into abutting engagement with the saddle opening shoulder surface 672c so that the saddle 520 is against or closely adjacent to the cap 518, as shown in FIGS. 41 and 42. In the compact arrangement, the double-ramped surface 800 is located within the cap opening 670 to hold cap 518 against the saddle 520.

The stop surfaces 688 at the terminal ends 681a, 681b of the stems 680a, 680b allow the cap 518 to remain in assembly with the saddle 520 in the event the cap 518 and saddle 520 are removed from the yoke 512, such as when a surgeon removes the fixation system 500 from a patient's spine.

More particularly, the ramp cam surfaces 800 include a lower cam surface portion 802 and an upper cam surface portion 804 that meet at a laterally common outer edge 806. Referring to FIG. 37, it can be seen that the intermediate outer cam surface edge 806 is sized approximately the same as the distance across the distal upper prong edge at 684a. As shown, the cam surface 802 is inclined away from axis 683 as it extends upwardly to edge 806 while the cam surface 804 is inclined toward the axis 683 as it extends upwardly from the edge 806. Thus, during assembly, the upper cam surface 804 can assist in shifting of the prongs 680a and 680b toward each other so they can fit through cap and saddle openings 670 and 672. Similarly, when turning of the cap 518 to loosen the saddle 520 on the rod 16, the upper cam surface 804 allows the saddle 520 along with the clip member 519 to be drawn back axially upward.

With the cap 518 and saddle 520 assembled as shown in FIG. 42, the edges 806 will be disposed in saddle opening upper portion 670b so that the lower ramp surface 802 frictionally bears on the surfaces about the opening lower portion 670a to hold the saddle upper surface 702 up against or closely adjacent the cap bottom surface 704. In addition, the ramped or inclined orientation of the cam surface 802 allows the saddle 520 to be driven downwardly or away from the axially stationary turning cap member 518. Turning of the cap member 518 toward its locked position causes the cam surfaces 802 to cammingly bear against the surfaces about opening portion 670a urging the resilient prongs 680a and 680b toward each other to allow the prongs including the edges 806 thereof to fit through the opening portion 670a. However, the axial distance between the cam surface edges 806 and the stop surfaces 688 is larger than the axial extent of the lower opening portion 670a of the saddle so that once the edges 806 clear the bottom of the opening portion 670a, the prongs 680a and 680b will be able to resiliently return toward their undeformed configuration so that the stop surfaces 688 are in interference with the seating surface 674 in the opening 670. In addition, with the saddle member 520 shifted axially downward, the cam surface edges 806 will be exposed out from the openings 670 and 672, as shown in FIG. 44.

Figure 39:
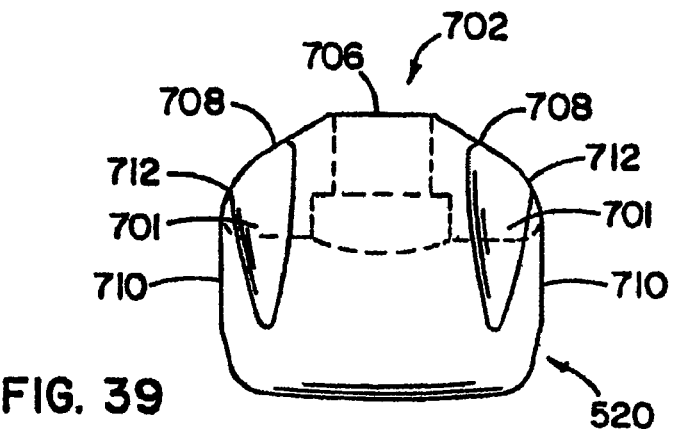
FIG. 39 is a side view of the clamping member rotated ninety degrees from the FIG. 38 view showing a pair of guide channels on one sidewall portion thereof.
Figure 40:
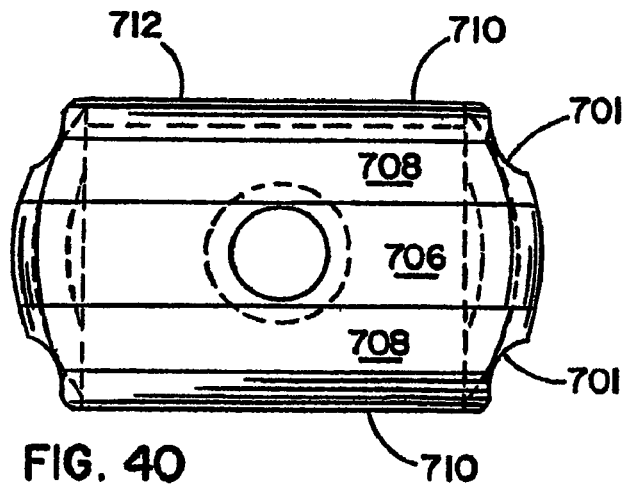
FIG. 40 is a plan view of the clamping member showing a through opening in the saddle member for the spring clip connector member.

As can be seen in FIGS. 38-40, the saddle 520 has grooves 701 along its sides 710. As mentioned above, when the saddle 520 is inserted into the yoke 512, as seen in FIG. 29, the grooves 701 receive the nub guides or detents 643 of the yoke 512, which direct the proper positioning and insertion of the saddle 520 within the yoke 512 with the yoke sides 710 guided along the interior of the yoke sidewall portions 604 and 606. The saddle 520 further has tapered ends 703, as can be seen in FIG. 38, which assists in moving the saddle 520 into or out of the yoke 512.

In addition, the bottom surface 700 of the saddle 520 is concave to engage the rod 16 in a complementary fashion. The saddle 520 also includes a distinctly profiled upper or top surface 702 designed to cooperate with a distinctly profiled bottom surface 704 of the cap 518 to cammingly shift the bottom surface 700 of the saddle 520 into locking engagement with the rod 16. More specifically, the top surface 702 of the saddle 520 has a generally horizontal and substantially flat portion 706 extending lengthwise toward each yoke sidewall portion 604 and 606 in a direction generally orthogonal to the direction of the axis 524 of the rod 16. In this regard, the saddle 520 presents an elongate cam surface 702 that is oriented ninety degrees from the elongate cam surface presented by the surface of the rod such as in the previously described system 10.

When the saddle 520 is deployed in the locked position with the cap 518, as seen in FIG. 44, force between the cap and saddle 520 is generally transmitted through the bottom cam surface portions 820 generally positioned at lateral positions 709 of the saddle top surface 702. The positioning of the saddle 520 transversely to a rod received in the bottom surface 700 thereof allows the saddle 520 to distribute locally the forces resolved through its lateral portions to a surface contact area in a local region of the rod 16. In contrast, were the saddle 520 oriented along the longitudinal axis 16a of the rod 16, or ninety degrees shifted from that depicted, the saddle 520 providing force through its lateral ends 709 would transmit the forces through a pair of local regions disposed along the top of the surface of the rod 16 mating therewith. Such arrangement may cause fretting, or damage and wear, to the rod 16 which may lead to failure of the rod or shearing of rod and saddle fragments. Furthermore, such an arrangement may impart a stiffness to a length of the rod 16 that is undesirable for the performance of the system when the patient is permitted to move, which places stress on the system.

The top surface 702 also includes two substantially flat side cam surfaces 708 flanking and meeting the flat portion 706. Each of the cam surfaces 708 is inclined from the flat portion 706 down to lower sides 710 of the saddle 520. The edge 712 between the cam surfaces 708 to the lower sides 710 is slightly rounded to allow the cap 518 to cam easily against the edge 712. Accordingly, the faceted cam surface 702 extends about an axis that is generally normal to the rod axis 16a.

Although the top surface 702 could, alternatively, be arcuately sloped upward for receiving the bottom cam surface 704 of the cap 518, the flat portions 706 provide a preferable distribution of stress during camming action. More specifically, a round or arcuate cam surface requires a significant amount of work to be done by the camming engagement in the initial portion of the arcuate cam surface, and then that amount of work decreases as the cam engagement travels up to the top of the arcuate cam surface.

In contrast, generally flat surfaces, such as flat portions 706, provide that the work is more evenly distributed along the flat portion 706 as the mating cam surface 704 of the cap 518 is directed over the flat portions 706.

Upon rotation of the cap 518 relative to the saddle 520, the bottom surface 704 of the cap 518 cams against the top surface 702 of the saddle 520 so that the bottom surface 704 of the cap 518 engages the top surface 702 of the saddle 520, which shifts the saddle 520 axially away from the cap 518 and into a tight engagement with the spinal rod 16. In this regard, the cap 518 itself does not shift vertically along and within the yoke 512, instead only rotating around its central vertical axis, as the cap 518 is turned for locking of the spinal rod 16. As previously discussed, the length 690 of the clip 519 between the base portion 680 and the stop surfaces 688 are designed specifically to allow this shifting operation between the cap 518 and the saddle 520.

As depicted in FIG. 34, the bottom surface 704 of the cap 518 is a programmed cam surface in the same manner as the cam lock member 18 discussed above and depicted in FIGS. 8 and 10, albeit shifted ninety degrees therefrom on the cap 518 so that in the unlocked position of the cap 518, as shown in FIG. 34, the cap cam surface 704 generally extends about an axis normal to the rod axis 16a. This is because the cam surface 702 of the saddle 520 is rotated ninety degrees from that of the rod surface as previously mentioned so that the corresponding cam surface portions of the cap cam surface 704 are also shifted ninety degrees from their location on the previously described cam lock member 18, as can be seen best in FIG. 34. This also allows the cam surfaces 702 and 704 to seat in close fitting relation prior to turning of the cap 518 toward its locked position so that the cap 518 and saddle 520 have a low profile in the yoke 512 with side portions of the cap 518 extending down about the saddle 520, as can be seen in FIG. 20. Accordingly, turning the cap member 518 toward its locked position will generate a camming action on the faceted cam surface 702 of the saddle 520 in much the same manner as the cam member 18 does on the rod 16 as discussed earlier. In addition, the bottom surface 704 includes additional cut-away recesses 720, depicted in FIG. 41.

The recesses 720 are located on an interior portion of ramp surfaces 108, 110 and serve to reduce wear and deformation of the ramp surfaces 108, 110 when rotated along the saddle cam surface 702. In contrast to the cam lock member 18 discussed above, the cap cam surface 704 includes a flat central portion 704a against which the top surface 706 rests when the saddle 520 and cap 518 are in the compact configuration of FIG. 42.

Figure 35:
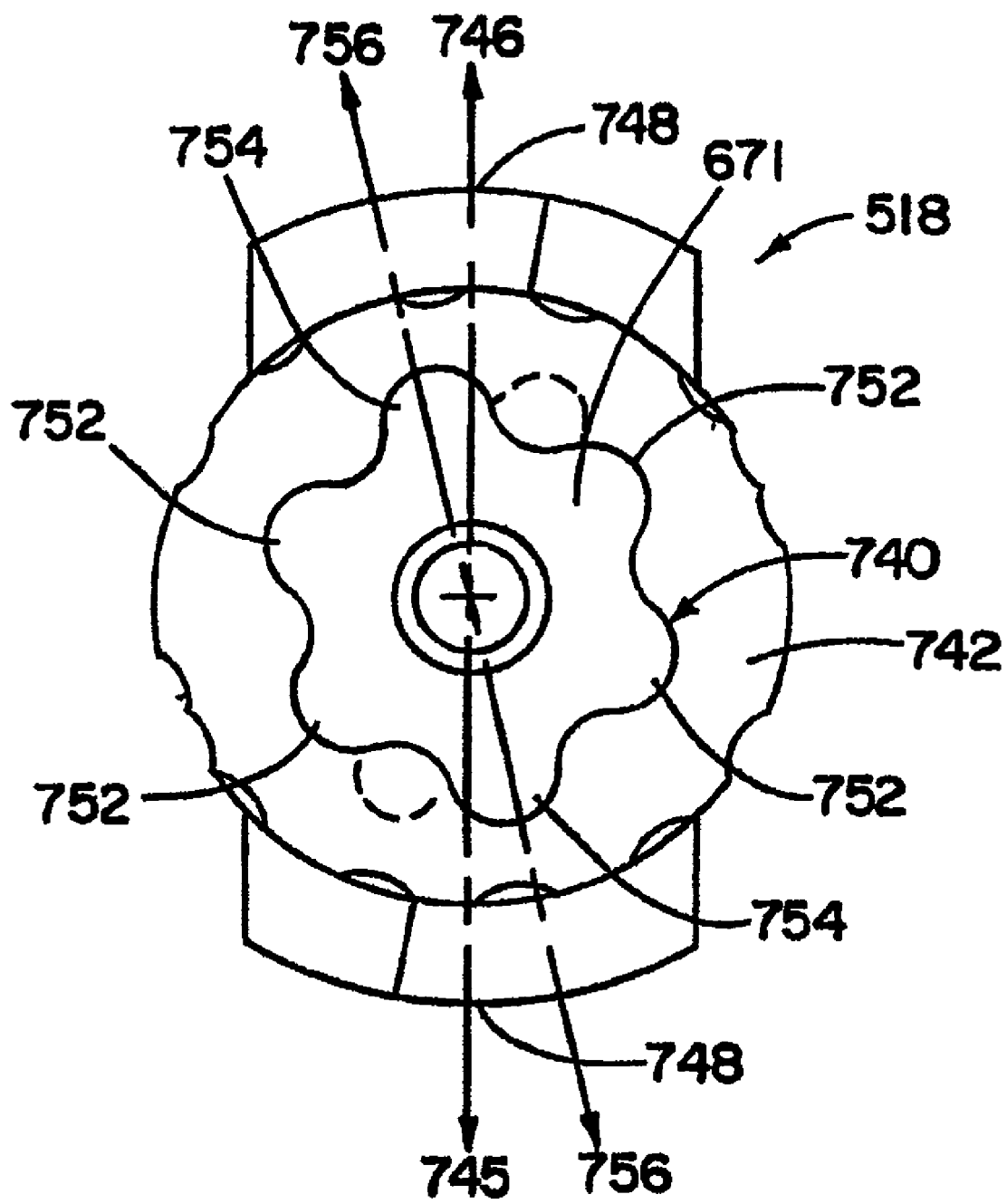
FIG. 35 is a plan view of the cam lock member showing a drive socket including asymmetric drive surfaces.

Referring now to FIG. 35, the cap 518 further includes a socket 740 for receiving a driver or a portion of a rod persuader. The cap 518 has a top surface 742, a central axis of rotation 744, and a central laterally extending axis 746. The central axis of rotation 744 and the central vertical axis 21 of the yoke 512 are generally aligned and coincident (see FIGS. 41 and 19). The lateral axis 746 is drawn along the midpoints 748 of each flange 656 intersecting the rotary axis 744 at the center of the socket 740. The socket 740 in the present form has a plurality of lobes 752 including a pair of lobes 754 which have a size larger than the other lobes 752 so that the lobes 752 are generally asymmetric about the socket 740. In addition, the larger lobes 754 are diametrically opposed and oriented along an axis 756 perpendicular to the axis of rotation 744 and angularly shifted from the central lateral axis 746, preferably by approximately 10 degrees. The geometry of the lobes 752 and 754 provides a driver or rod persuader received by the receptor 740 with only two distinct mating positions, and the offset axis 756 of the lobes 754 provides a surgeon an indication of the position of the cap 518 relative to the driver or rod persuader.

It should be noted that the lobes 752, 754 could be arranged and located in a plurality of orientations provided the cap 518 and instrument have, preferably, only one relative orientation therebetween for mating. Although the preferred embodiment includes the lobes 752 and 754, other geometry may be employed. The lobes 752 and 754, however, enable greater torque to be used between the cap 518 and driver than other known geometries.

Figure 45:
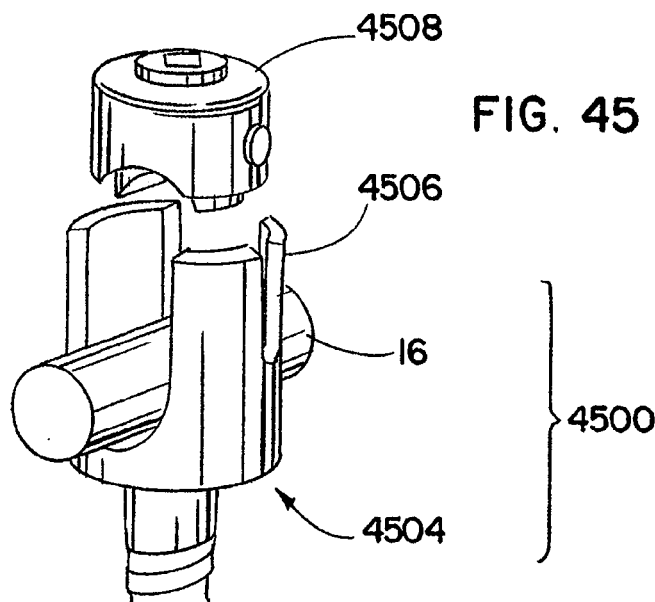
FIGS. 45 and 46 are partially exploded perspective views of another form of the spinal fixation system in accordance with the present invention.
Figure 46:
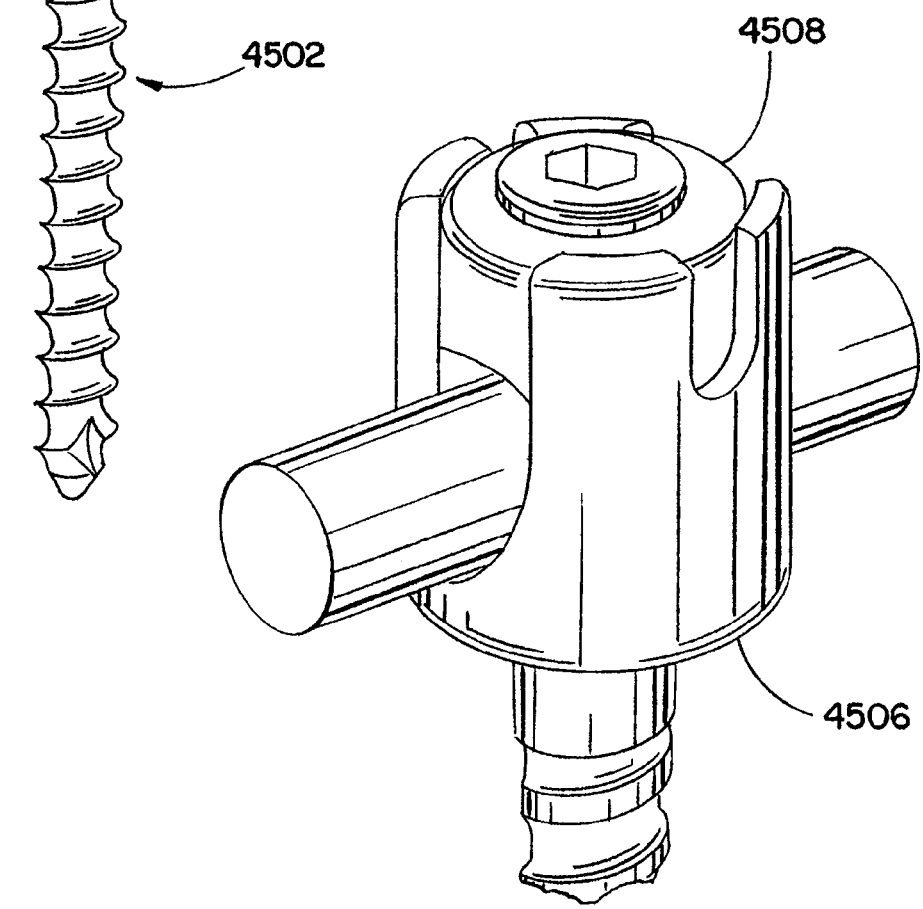

Referring now to FIGS. 45-51b, a spinal fixation system 4500 for securing a spinal rod 16 in accordance with another form of the present invention is depicted. As can be seen in FIGS. 45 and 46, the system includes a bone anchor member such as screw 4502 and a coupling device 4504 for securing the spinal rod 16 relative to the bone screw 4502. The coupling device 4504 includes a coupling member in the form of a unitary yoke 4506 and as shown previously an insert in the form of an anvil 516, and a cam lock member 4508.

Figure 47:
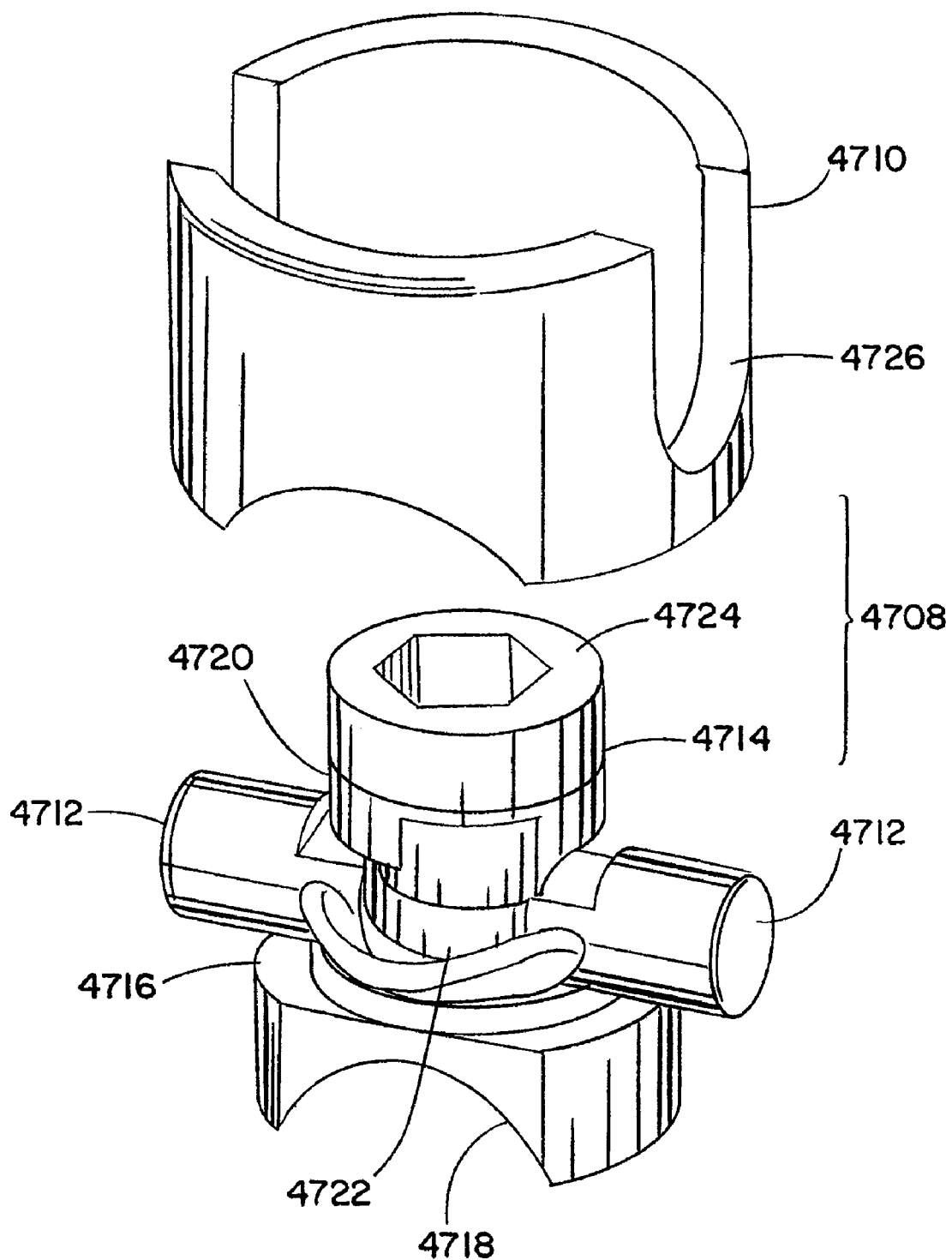
FIG. 47 is a partially exploded view of the cam lock member depicted in FIG. 45.
Figure 48:
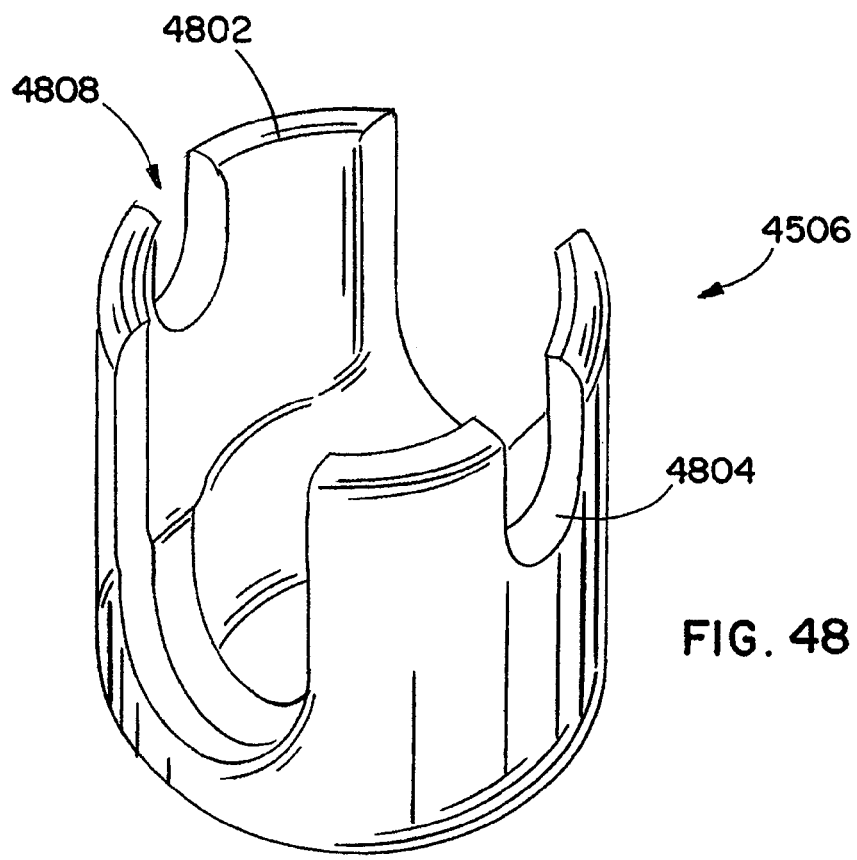
FIG. 48 is a perspective view of the coupling device depicted in FIG. 45.

In FIG. 47, the cam lock member 4508 is in the form of a cap 4710, a pair of cam bars 4712, a cam post 4714, a biasing element 4716, and a saddle 4718. The cap 4710 may house several internal components and is shaped to fit in a bore 4802 of the unitary yoke 4506. The unitary yoke 4506 may include cam bar recesses 4804 to house the cam bars 4712. The unitary yoke 4506 may also include cam bar guides 4808 to guide the cam bars 4712 into the cam bar recesses 4804.

The cap 4710 is shown having an outer circular profile, however, since the cap 4710 is not required to rotate, it may have any variety of non-circular profiles preferably complementing the profile of the bore 4802. The cap 4710 and bore 4802 preferably have a profile which permits insertion of the cap 4710 into the bore 4802 of the unitary yoke 4806. Each embodiment of the cam lock member 4508 may include a drive feature 4724 which may be in the shape of a hex, or other non-circular profile. The drive feature 4724 may be recessed or in the form of a boss.

Figure 49:
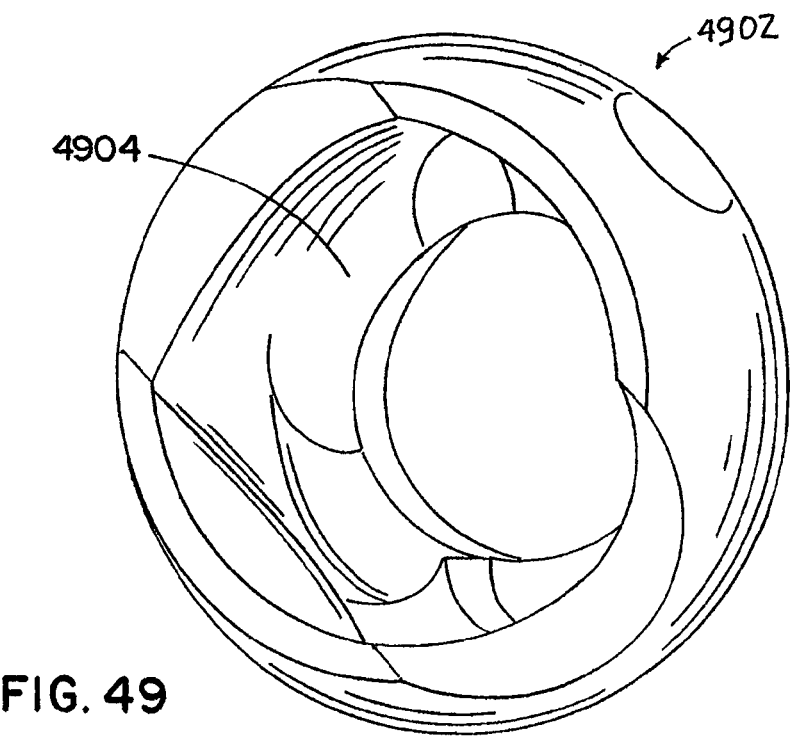
FIG. 49 is a perspective view of an alternative form of the cap depicted in FIG. 47.

The cap 4710 may assume a profile which permits it to pivot generally about the axis of the cam bars 4712 within the bore 4802. For example, FIG. 49 shows a cap having a rounded or spherical outer surface shaped to permit pivoting about the axis of the cam bars 4712. Some caps of the prior art overly constrain a segment of the spinal rod lying directly under the cam lock member. This over constraint can cause amplified stresses in the spinal rod and lead to spinal rod failure especially with repetitious forward flexion and extension motion. A pivotable profile of the cam lock member 4508 permits it to conform to the natural bending of the spinal rod that occurs during loading thereby serving to lower spinal rod stress. Any range of pivoting motion of the cap 4710 is helpful to reduce the spinal rod stress particularly in the range of 0-20 degrees from neutral in either direction. Therefore, any complementary geometry between the cap 4710 and the bore 4802 that permits this pivoting motion falls within the scope of this invention. For example, the outer diameter of the cap 4710 may simply be slightly undersized, rather than rounded, with respect to the bore 4802 diameter to permit this pivoting motion.

The cap 4902, 4710 may include one or more rod locking ramps 4904. These rod locking ramps 4904 interface with one or more coinciding rod locking lobes 4720 or ramps on the cam post 4714 wherein rotation of the cam post 4714 causes the cam post 4714 to move toward the spinal rod 16 for clamping purposes. Clearly the ramps 4904 and rod locking lobes 4720 may take other forms such as cams as long as the interaction between them causes the cam post 4714 to move toward or permits it to move away from the spinal rod.

Figure 52:
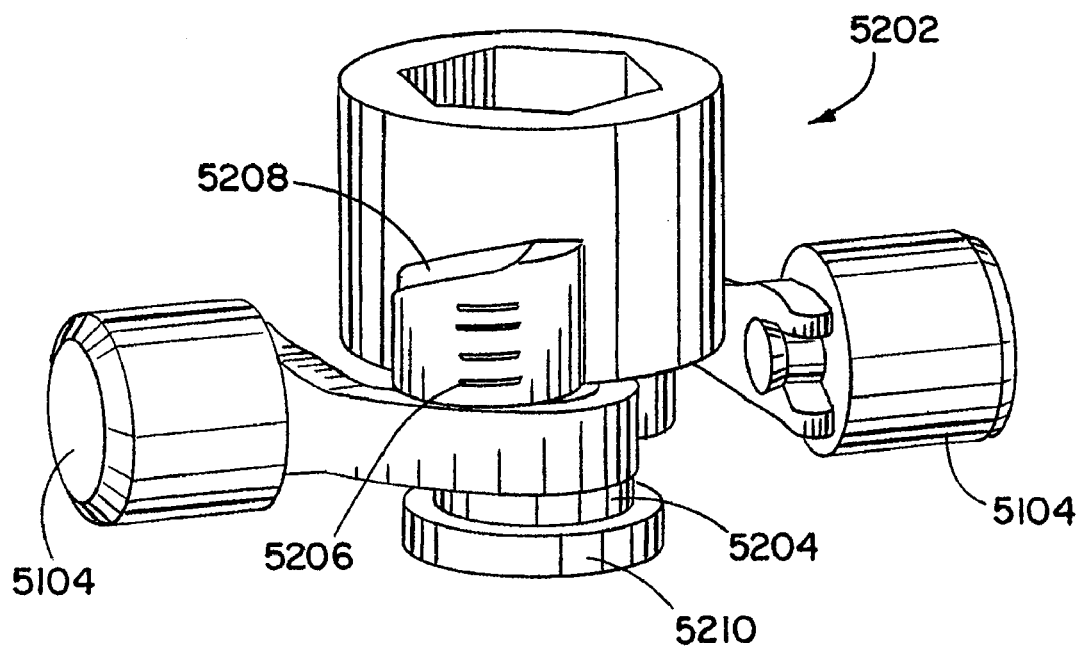
FIG. 52 is a perspective view of the internal structure of an alternative form of the cam lock member (cap removed) in accordance with the present invention.

The cam post 4714 may also include one or more bar locking lobes 4722. The bar locking lobes 4722 secure the cam bars 4712 in the locked position upon rotation of the cam post 4714. Additionally, if so configured, the bar locking lobes 4722 may force the cam bar 4712 to be deployed out into the unitary yoke 4506. The positioning of the bar locking lobe 4722 on the cam post 4714 may vary. For example, FIG. 52 illustrates a bar locking lobe 5206 that is positioned on a surface lateral to the rod locking ramp 5208. As a cam post 5202 is rotated to the locked position, the bar locking lobe 5206 positions itself behind a cam bar 5104 thereby blocking its retraction from the cam bar recess 4804.

The cam lock member 4508 may include a spinal rod saddle 4718, spinal rod boss, or other rod contact surface portion 5210 to transmit locking force to the spinal rod 16. The cam bars 4712, 5104, may include one or more biasing elements 4716 to bias the cam bars 4712 either toward or away from the cam post 4712. It is preferred the biasing element 4716 be in the form of a spring wire or band, or coiled spring. The biasing element may alternatively be integral to the cam bar 4712 rather than a separate part.

A biasing element 4716 that is configured to bias the cam bar 4712 outward will provide the benefit of the cam lock member 4508 to be simply pushed into the unitary yoke 4506, to obtain the initial locked capture of the spinal rod 16 since the cam bars 4712, 5104 will be pre-biased and captured into the cam bar recess 4804. For removal of the cam lock member 4508, the cam post 4714 is derotated to the unlocked position, and an instrument fit preferably over the outside of the unitary yoke 4506, having a boss or other protrusion to fit into the cam bar recesses 4804, may be used to retract the cam bars 4712 from the cam bar recess 4804. This cam lock member removal instrument may then retract the cam lock member 4508 from the unitary yoke 4506. The unitary yoke members 4506 may therefore include structure on an outer surface such as a boss, recess, or flange, to assist the removal instrument in capturing the cam lock member 4508.

A biasing element 4716 that is configured to bias the cam bar 4712 inward may rely on the rotation of the cam post 4714, specifically the bar locking lobe 4722, to deploy the cam bar 4712 into the cam bar recess 4804. In this embodiment, the cam bars 4712 will self-retract from the cam bar recess 4804 when the cam post 4714 is derotated to the unlocked position.

FIG. 51A illustrates an alternative biasing element 5102. This biasing element 5102 takes the form of a shaped elongated band having a portion fastened, connected, fixed, or otherwise contacting the cam bar 5104 and another portion fastened, connected, fixed, or otherwise contacting the cam post 5202. In this embodiment, the biasing element 5102 is shaped to wrap around a cylindrical shaft portion 5204 of the cam post 5202. As a further alternative, the cam bars 4712 may be equipped with a blind bore which houses a resilient element such as a spring. One end of this spring will push the cam bar 4712 outward, whereas the other end of the spring will be biased against the shaft portion 5204 of the cam post 5202.

Figure 51B:
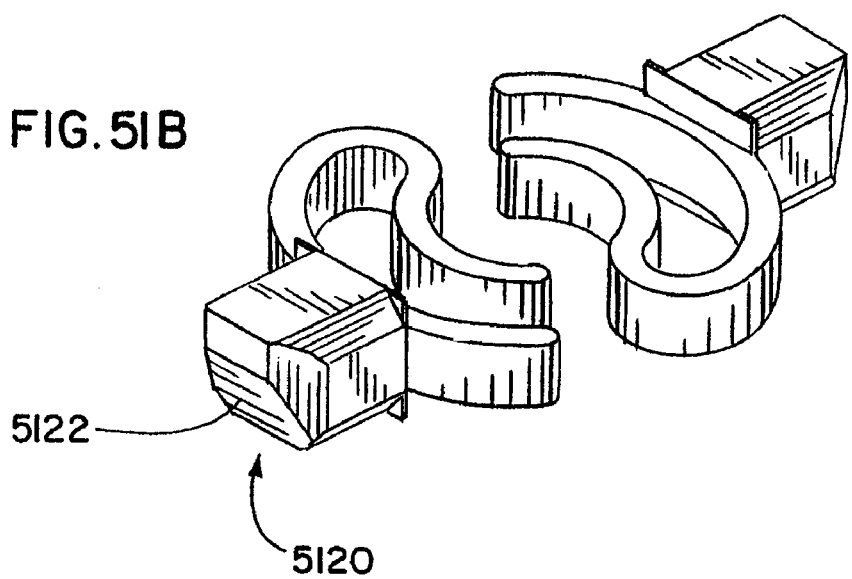
FIG. 51B is a perspective view of an alternate profile for a cam bar.
Figure 51C:
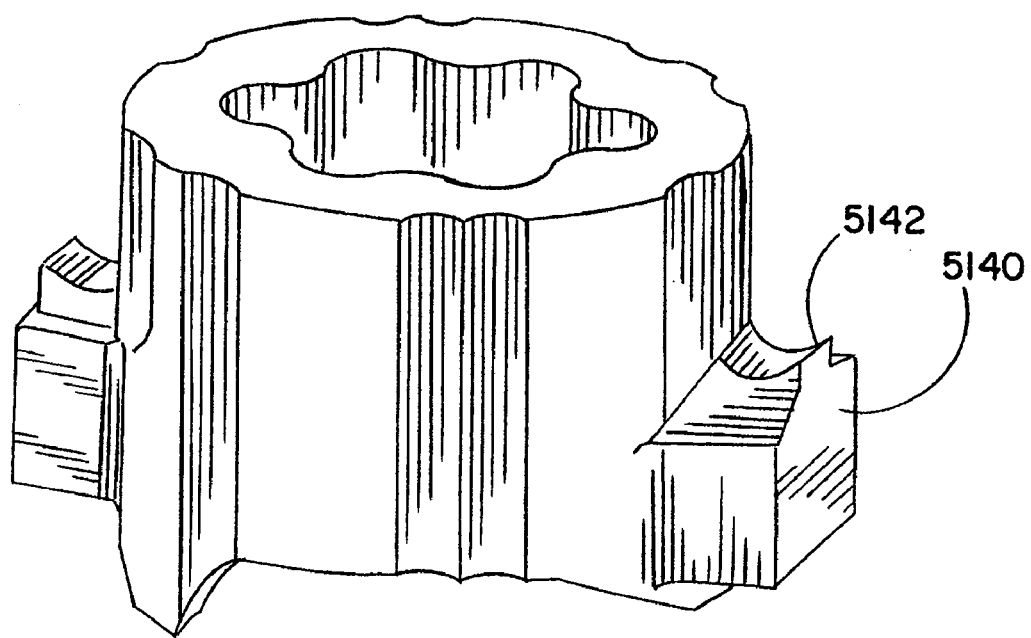
FIG. 51C is a perspective view of an alternate form of the cap shown in FIG. 33 in accordance with the present invention.

The cam bars may have a variety of profiles. For example, cam bar 5120 may have a chamfered face 5122 to encourage easy insertion into the unitary yoke 4506. This chamfered face 5122 portion may be used as a substitute or in conjunction with the cam bar guide 4808. Further, any one of the faces of the cam bar 4712 may be rounded or chamfered. This applies equally to the cam lock members shown previously such as in FIG. 33. FIG. 51C illustrates a cam lock member similar to the cam lock member of FIG. 33 but with the radial flanges 656 replaced by the protruding boss 5140. This boss 5140, like any of the cam bars described in this disclosure, may include a flange portion 5142 for reception in a recess portion, such as illustrated in FIG. 6 as recesses 104 and 102, to prevent splaying of the unitary yoke 4506.

Figure 51D:
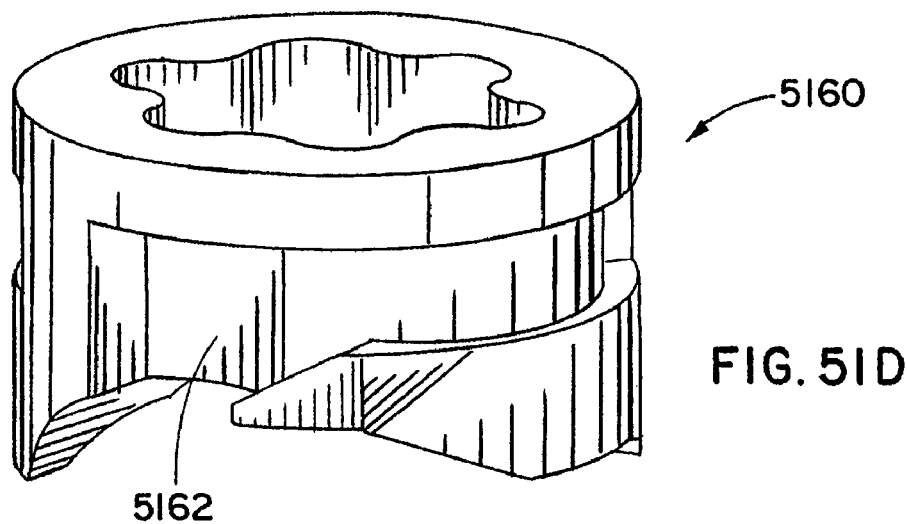
FIG. 51D is a perspective view of an alternate form of the cap shown in FIG. 33 in accordance with the present invention.
Figure 51E:
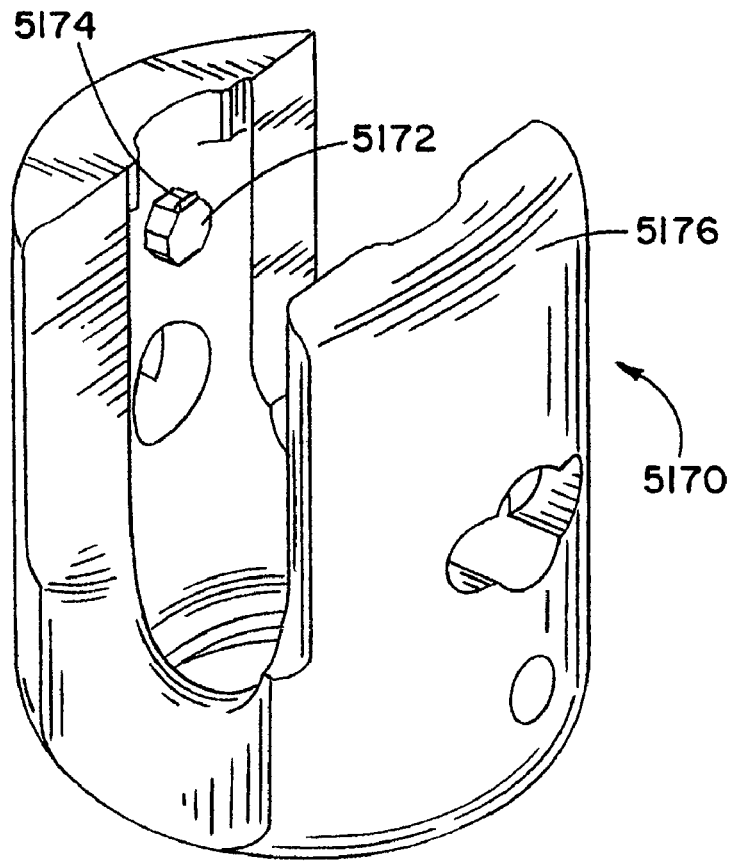
FIG. 51E is a perspective view of an alternate form of the yoke in accordance with the present invention.
Figure 51F:
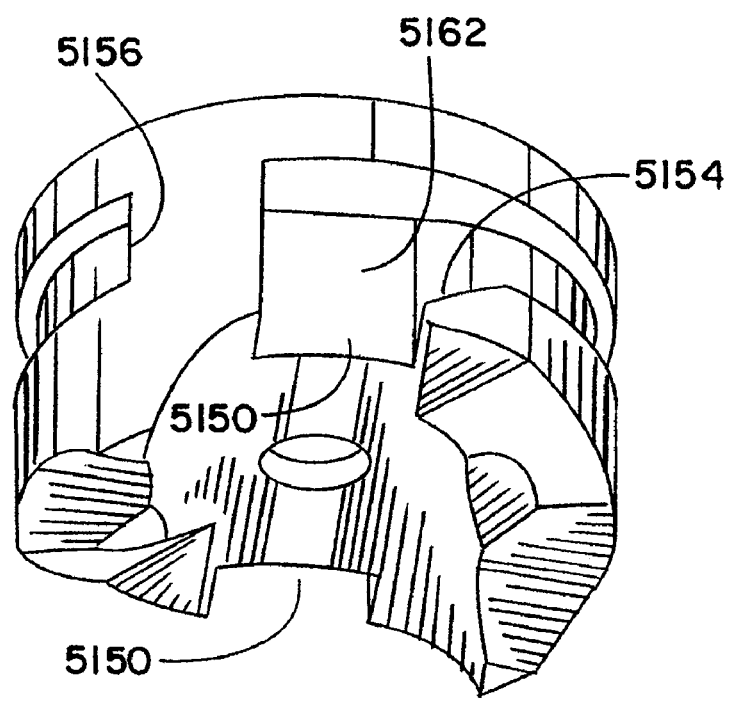
FIG. 51F is a perspective view of the cap shown earlier in FIG. 51D.

In another embodiment, the cam lock member in FIG. 33 may be absent of radial flanges 656, protruding bosses 5140, or other protruding retention features. For example, as shown in FIGS. 51D-F, these features may be omitted in favor of a cap 5160 having a generally L-shaped groove 5162. In this manner, it is preferred that the yoke 512 of FIG. 20 be modified such that the recesses 642 are removed and replaced by a peg or boss 5172 such as shown in yoke 5170 in FIG. 51E. This peg or boss 5172 may include a flange portion 5174 which cooperates with a recess (not shown) in the upper wall of the generally L-shaped groove 5162 to prevent splaying of yoke walls 5176 of the yoke 5170. Clearly, the flange portion 5174 could alternatively be a recess given there is a cooperating flange-like structure on an upper wall of the generally L-shaped groove 5162. It is preferred that the peg or boss 5172 is also mirrored on the opposing yoke walls 5176. Upon insertion of the cap 5160 into the yoke 5170, the peg or boss 5172 will enter the groove through the groove entry 5150. The generally L-shaped groove 5162 may include chamfered, radiused, or other broken edges 5154 to smoothly introduce the peg or boss 5172 into the groove 5162. The generally L-shaped groove 5162 may include ridges, bumps, flats, or other structure to provide a positional feel to intermediate locking positions of the cap 5160. The cap 5160 may have a generally L-shaped groove 5162 path of just less than 180 degrees. For example, the groove 5162 shown spans 162 degrees. The groove end 5156 of the groove 5162 may adequately serve as a distinct stop to rotation providing a clear signal to the user that the cap 5160 is fully locked. Note that since the groove 5162 is flat, rotation of the cap 5160, with peg or boss 5172 within groove 5162 does not cause the cap 5160 to advance toward the spinal rod 16. Instead, it is the ramp surfaces 108, 110, that advance the saddle 520 toward the rod 16 to fix the rod 16 in place. As an alternative, the cap 5160, or below-described caps 5180 and 5110, may include underside ramping such as shown in FIG. 8 with ramp surface regions 108 and 110 in place of a saddle 520.

Figure 51G:
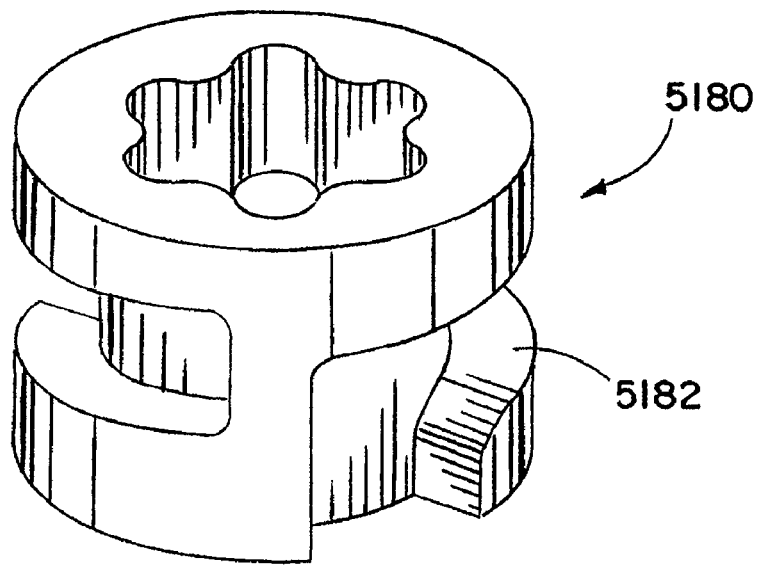
FIG. 51G is a perspective view of an alternate form of the cam lock member.
Figure 51H:
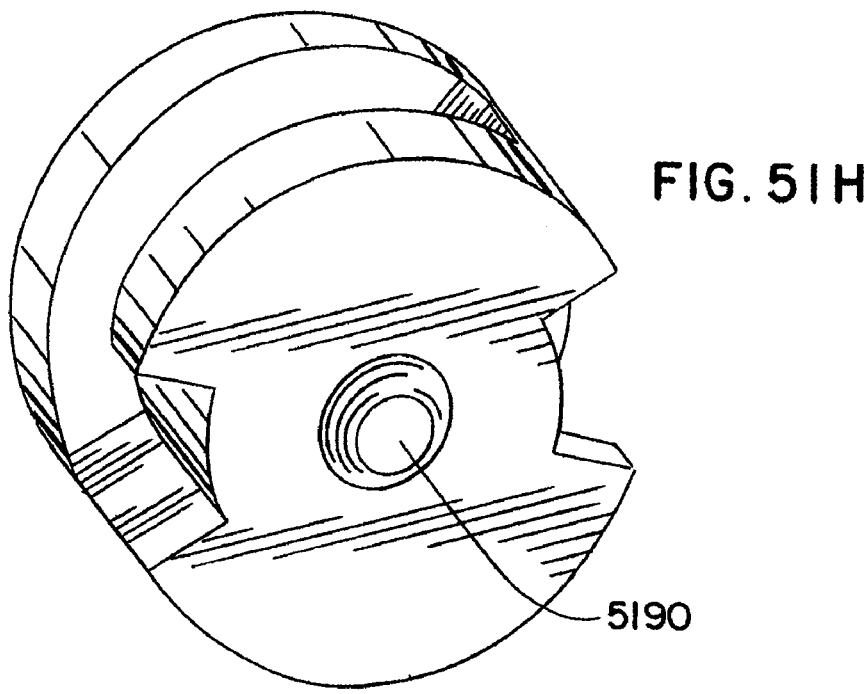
FIG. 51H is a bottom perspective view of the cam lock member in FIG. 51G.

In an alternative embodiment shown in FIG. 51G, the cap 5180 comprises a sloped groove 5182. Rotation of the cap 5180, with peg or boss 5172 within groove 5182, causes the cap 5180 to advance toward the spinal rod 16. In this instance, the cap 5180 may comprise a boss, flat, face or other surface 5190 that is capable of applying a compression force on the rod 16 to fix it in a predetermined position. Alternatively, the face 5190 may be contoured in the shape of a saddle, such as saddle 4718, such that it may cup the spinal rod 16 and rotate relative to the cap 5180.

Figure 51I:
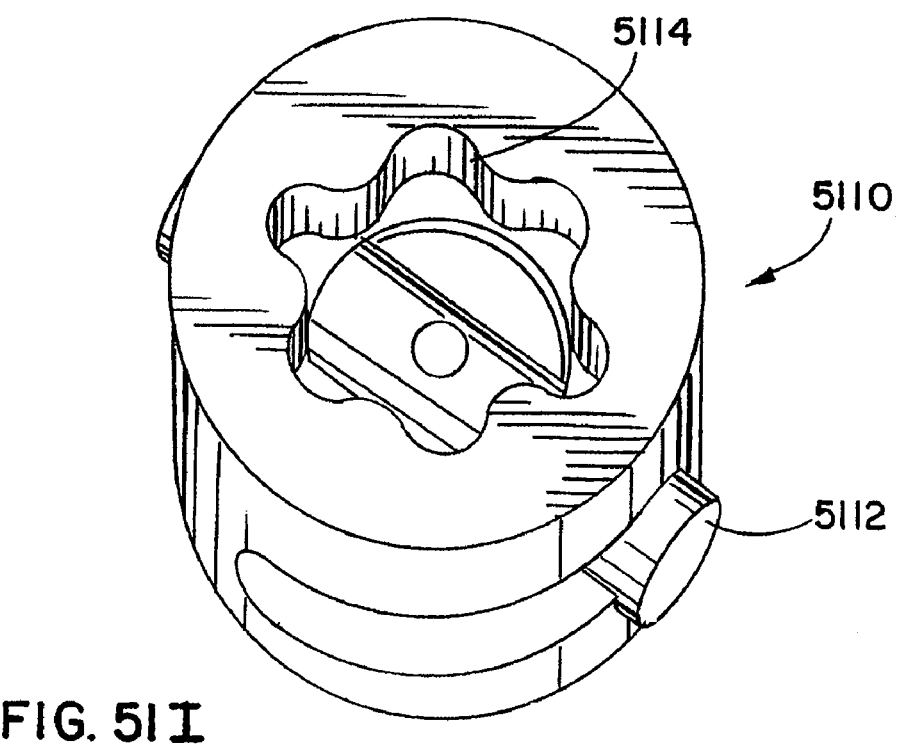
FIG. 51I is a perspective view of an alternate form of the cam lock member.
Figure 51J:
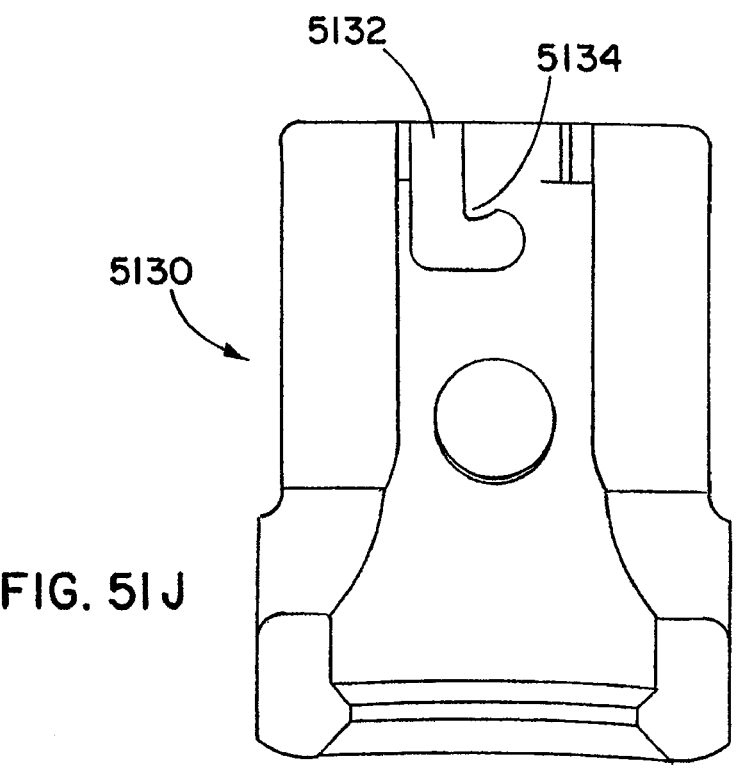
FIG. 51J is a cross-sectional view of an alternate form of the yoke showing one half of the structure.

In yet another embodiment illustrated in FIG. 51I, cap 5110 may utilize a pivoting bar 5112 to secure the cap 5110 within the yoke. An instrument (not shown), preferably cannulated with central arms to engage the pivot bar 5112, and preferably an outer sleeve that engages a drive 5114, is utilized to lower the cap 5110 into a yoke 5130 (one wall shown). The pivot bar 5112 is lowered down a J-slot 5132 and rotated slightly by the central arms of the instrument into the end of the J-slot 5132 to a secure position behind a retention boss 5134. The outer sleeve of the instrument which engages the drive 5114 is then rotated such that the cap 5110 is advanced towards and locks the spinal rod 16 within the yoke 5130. Again, this cap may comprise a boss, flat, face or other surface that is capable of applying a compression force on the rod 16 to fix it in a predetermined position. Alternatively, the cap 5110 may include the face 5190 which may be contoured in the shape of a saddle such as saddle 4718 such that it may cup the spinal rod 16 and rotate relative to the cap 5180.

Referring back to FIG. 47, it is preferred the cam lock member 4508 include features to limit its rotation from an unlocked and undeployed position, to a locked on cam bars 4712 and deployed on spinal rod 16 position, and positions therebetween. For example, the saddle may include cam stops 5002 (FIG. 50) that interfere with the cam post 4714 at the ends of these positional ranges. Similarly, this rotation limiting geometry could be on the unitary yoke 4506, the cam post 4714, or the cam bars 4712.

In a preferred embodiment, the relationship of the bar locking lobe 4722 to the rod locking lobe 4720 is important. For example, as the cam lock member 4508 is lowered into the bore 4802 of the unitary yoke 4506, it is preferred that the cam bars 4712 are locked into the cam bar recess 4804 of the unitary yoke 4506 before substantial locking force is applied to the spinal rod 16 by the cam lock member 4508. Therefore, upon rotation of the cam post 4714, the bar locking lobe 4722 may be positioned such that it blocks the cam bar 4712 from escaping the cam bar recess 4804 before the rod locking lobe or ramp 4720 causes substantial displacement of the cam post 4714 towards the spinal rod 16. However, continued rotation of the cam post 4714 causes continued displacement of the cam post 4714 toward the spinal rod 16 until it is fully locked down.

Figure 53:
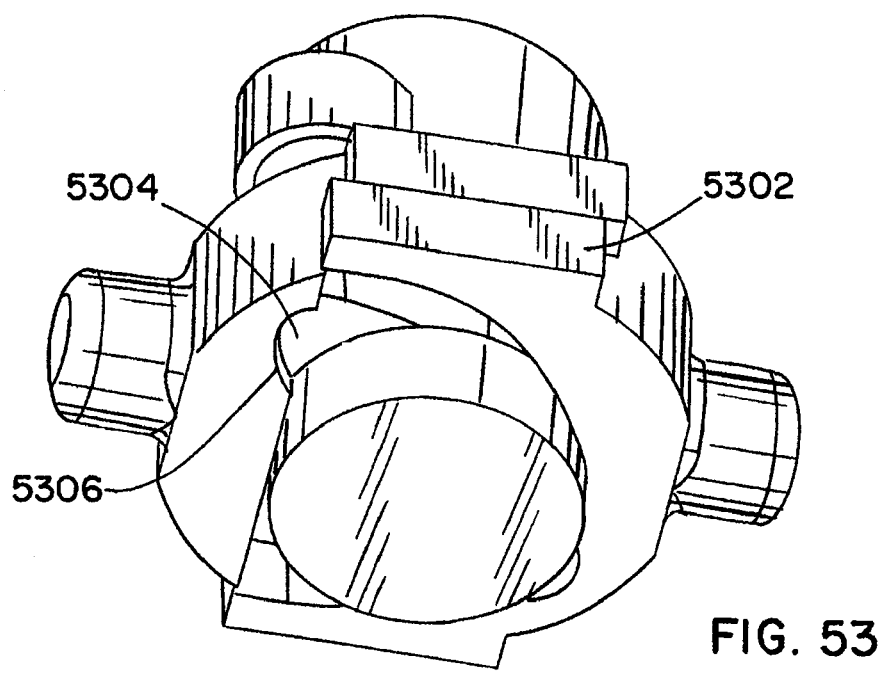
FIG. 53 is a perspective view of the internal structure of an alternative form of the cam lock member (cap removed) in accordance with the present invention.
Figure 54:
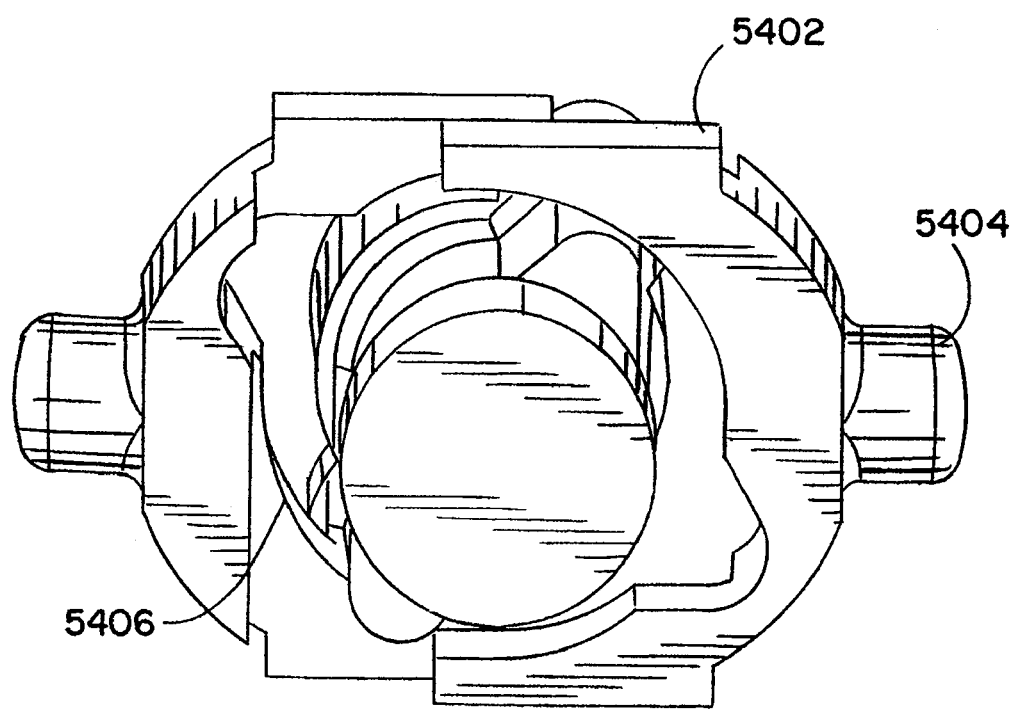
FIG. 54 is a perspective view of the structure shown in FIG. 53 but in its deployed and locked position.

In another embodiment of the cam lock member 4508, the cam bars 4712 may include a system of sliding, telescoping, or interlocked plates 5302. In FIG. 53 (cap 4710 removed), these plates are retracted on each other in a position suitable for passage of the cam lock member 4508 into the bore 4802 of the unitary yoke 4506. Note in this position, a bar locking lobe 5304 rests in a bar lock recess 5306. However, as the cam post 4714 is rotated, the sliding plates 5302 expand and as such cause cam bars 5404 to move into the cam bar recess 4804. The sliding plates 5302 may have a tongue and groove, telescoping, or other arrangement which helps keep the cam bars 5404 adequately concentric with the axis of the cam bar recess 4804. Note that the cam post 4714 may continue to be rotated along a bar lock wall 5406 until the cam post 4714 is fully displaced and the spinal rod 16 is locked down.

It is often an advantage for the spinal rod 16 to be initially captured between the cam lock member 4508 and the head of the screw 4502 within the unitary yoke 4506 before final lock down of the rod. In this case, the spinal rod 16 will be captured within the spinal fixation system 4500 while the surgeon will still have the opportunity to rotate the spinal rod 16 before final lockdown.

Figure 55:
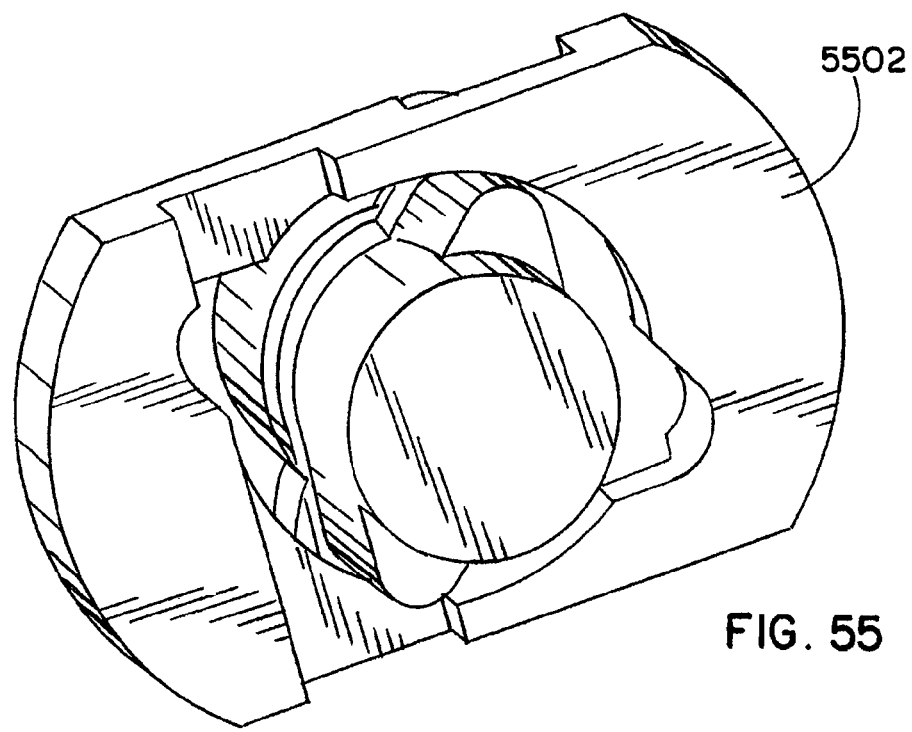
FIG. 55 is a perspective view of the internal structure of an alternative form of the cam lock member (cap removed) in accordance with the present invention.

The cam bar may have a variety of profiles. For example, as shown in FIG. 55, a cam bar 5502 is shaped in the form of a rectangular tongue which forms a broader surface of engagement with a cam bar recess similar to cam bar recess 4804. In this case, the cam bar recess would preferably be fashioned in a rectangular shape to coincide with the shape of the cam bar 5502.

Figure 56:
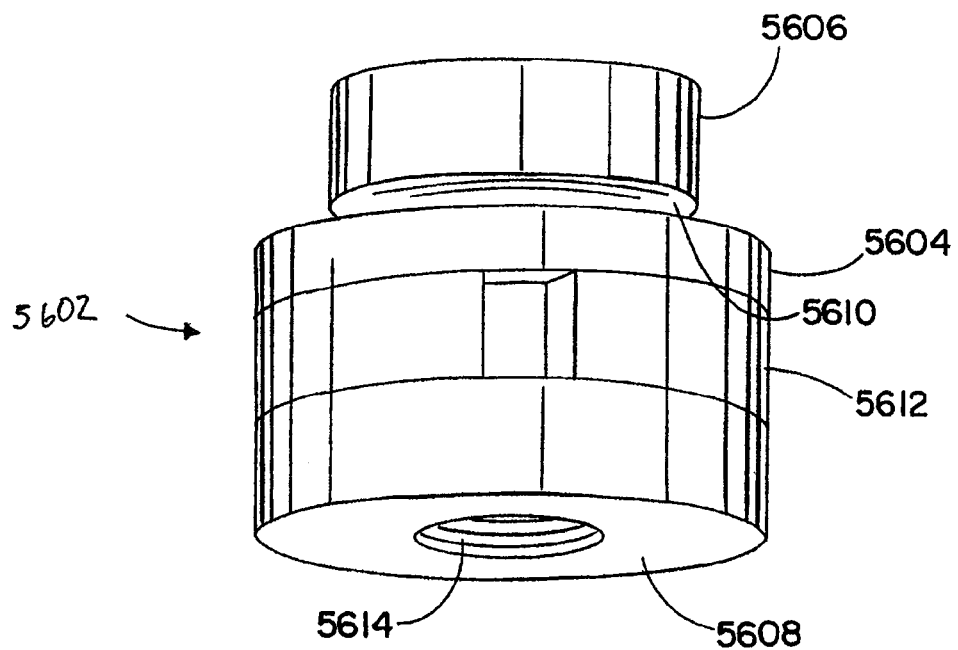
FIG. 56 is a perspective view of an alternative form of the cam lock member.
Figure 57:
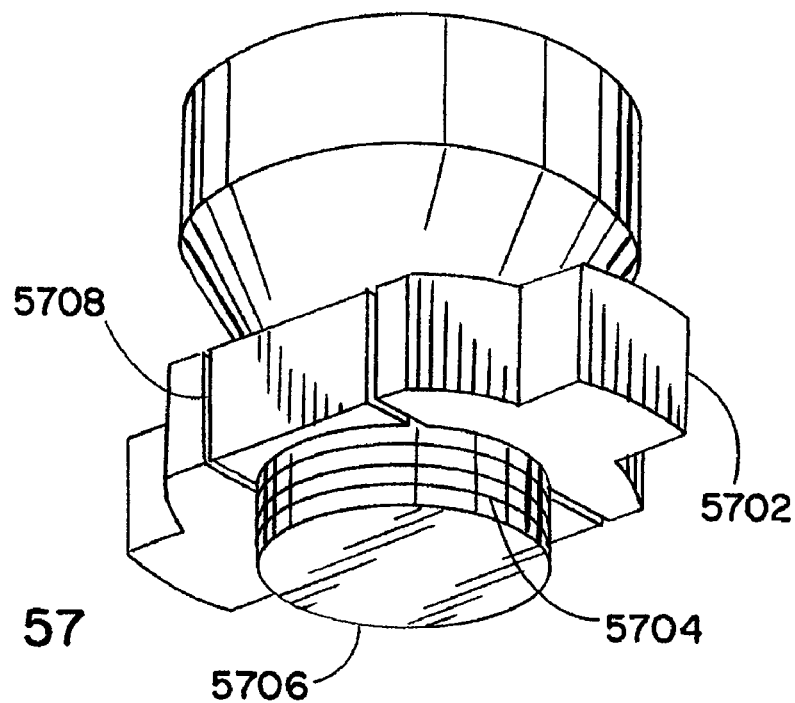
FIG. 57 is another perspective view of the structure in FIG. 56 but with cap portion removed.

Another embodiment of a cam lock member is shown in FIGS. 56 and 57. This cam lock member 5602 is comprised of a cap 5604 portion, a camming post 5606 portion, and a cam bar 5702 portion. The cam bar 5702 may rest on an inside surface of a cap floor 5608. The camming post 5606 may include a cam surface 5610 having the function of expanding or locking the cam bars 5702 through cap bar recesses 5612 and into a cam bar recess similar to cam bar recess 4804 of the unitary yoke 4506 as the camming post 5606 is rotated. The camming post 5606 shown includes threads 5704 at its distal end which mate with threads 5614 in a bore in the cap floor 5608. With continued rotation of the camming post 5606, a face 5706 of the camming post 5606 will compress the spinal rod 16 into a locked position. The length of the camming post 5606 may be precisely machined such that when the cam surface 5610 is fully engaged with and abuts the cam bars 5702, the system will have a discrete stop and optimal locking force will be applied to the rod. Alternately, a ridge (not shown) at the top of the camming post 5606 which jams the top of the cap 5604 at full locking will serve to provide the same discrete stop function.

In this embodiment, the cam bars 5702 are shown as a unitary part. The part may include resilient cuts 5708 to provide a spring-like expansion between the cam bars 5702 for deployment of cam bars 5702 into the cam bar recess of the unitary yoke. Alternatively, this portion may be replaced by small springs or a springy band. As described earlier, it is preferred that the cam bars 5702 be biased outward towards the bore 4802 or cam bar recess of the unitary yoke 4506. In this fashion, the cam lock member 5602 may have a push and click function wherein the cam bars automatically click into the yoke by the force of an instrument down the axis of the bore 4802. The surgeon can then make adjustments to the spinal rod 16 while the rod 16 remains captured in the yoke. When the camming post 5606 is rotated, the cam surface 5610 will hold the cam bars 5702 in the deployed position and the face 5706 of the camming post will advance to lock down the spinal rod 16.

Figure 58:
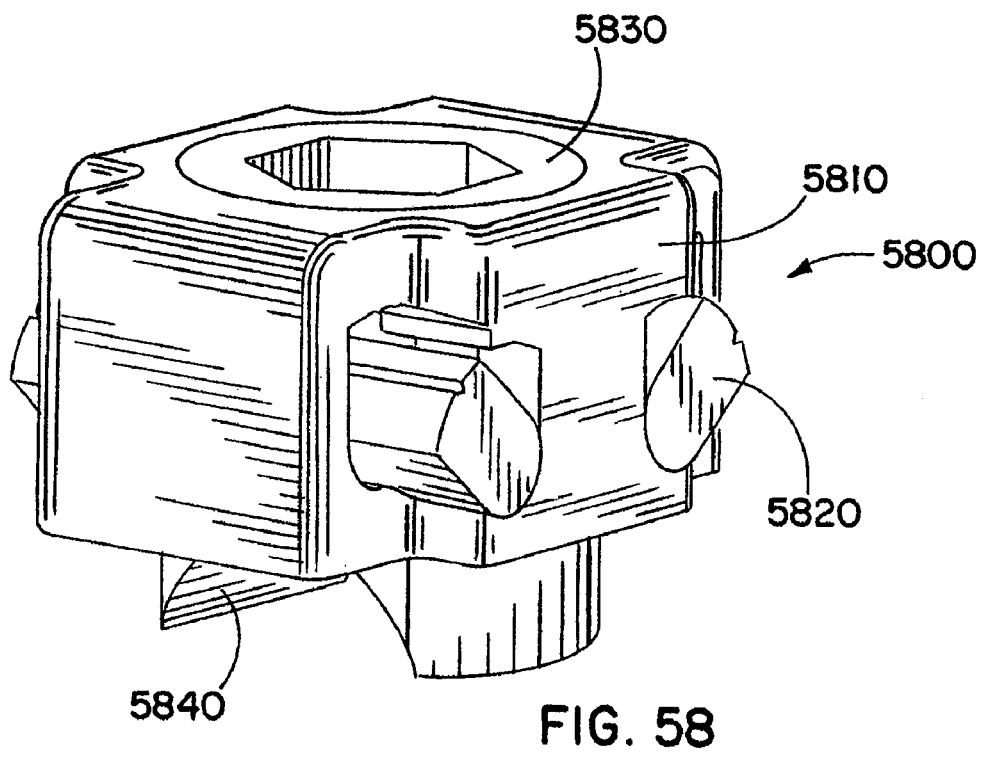
FIG. 58 is a perspective view of an alternative form of the cam lock member in accordance with the present invention.
Figure 59:
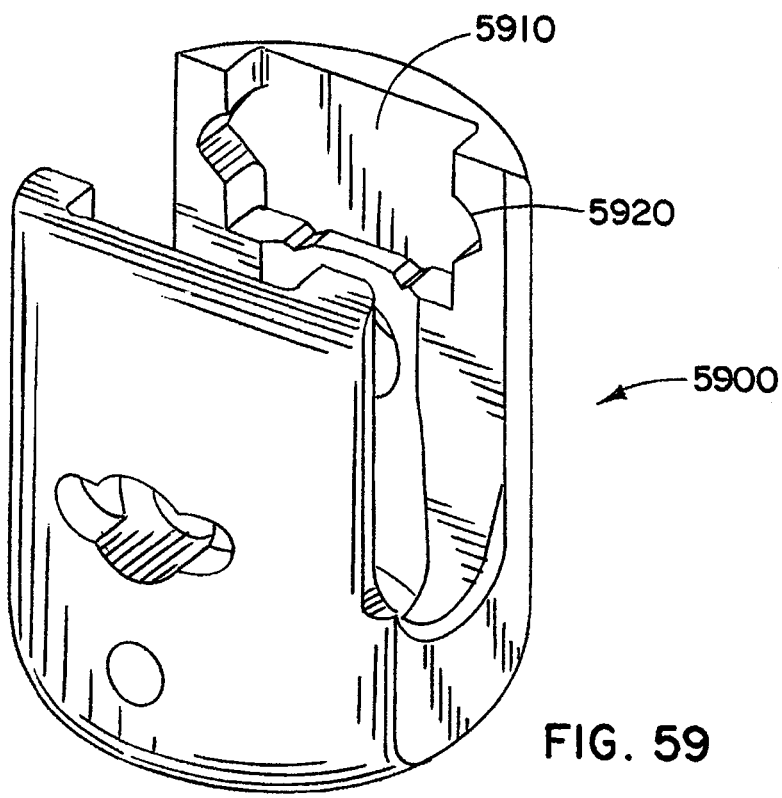
FIG. 59 is a perspective view of an alternative form of the yoke in accordance with the present invention.
Figure 60:
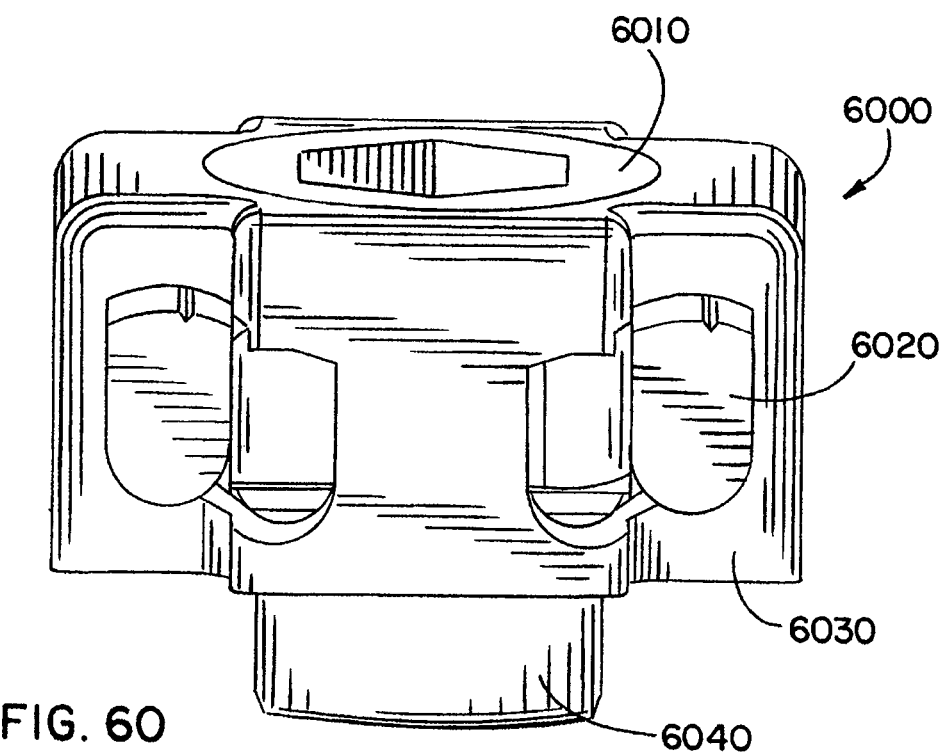
FIG. 60 is a perspective view of an alternative form of the cam lock member illustrated in FIG. 58.
Figure 61:
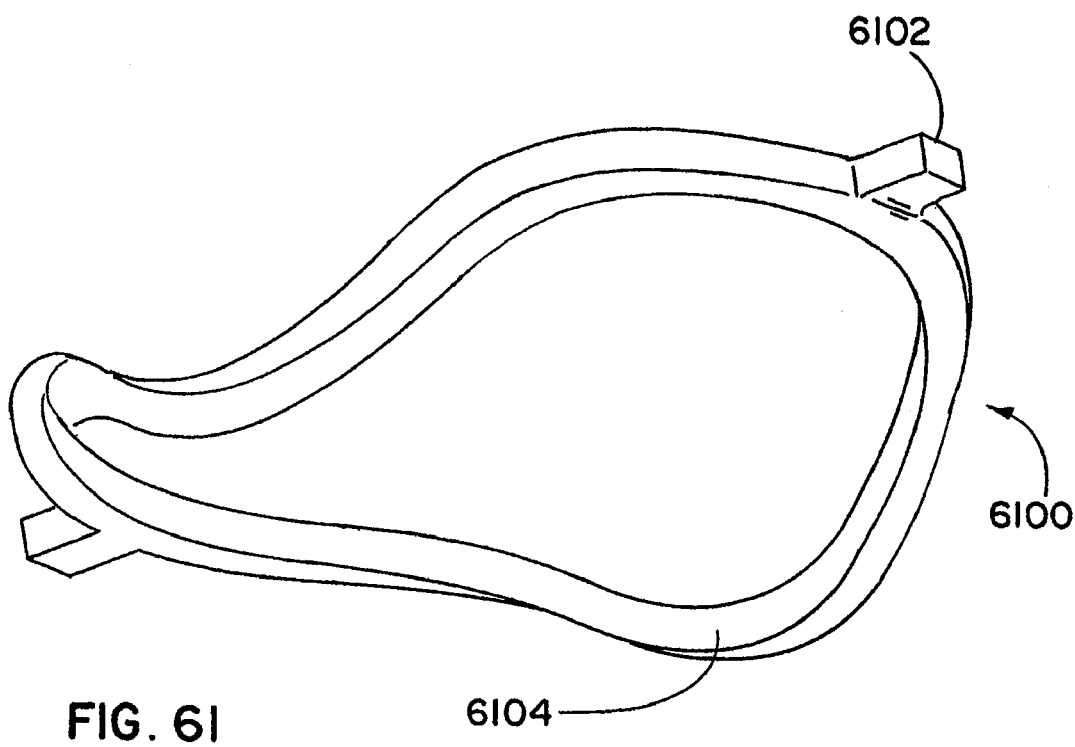
FIG. 61 is a perspective view of a gimble used to secure the screw and anvil subassembly in the yoke.
Figure 63:
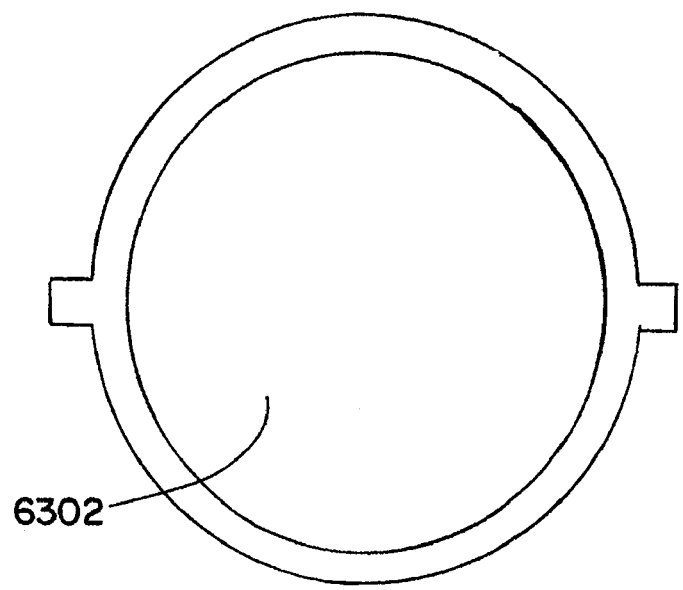
FIG. 63 is a top view of the gimble in FIG. 61.
Figure 62:
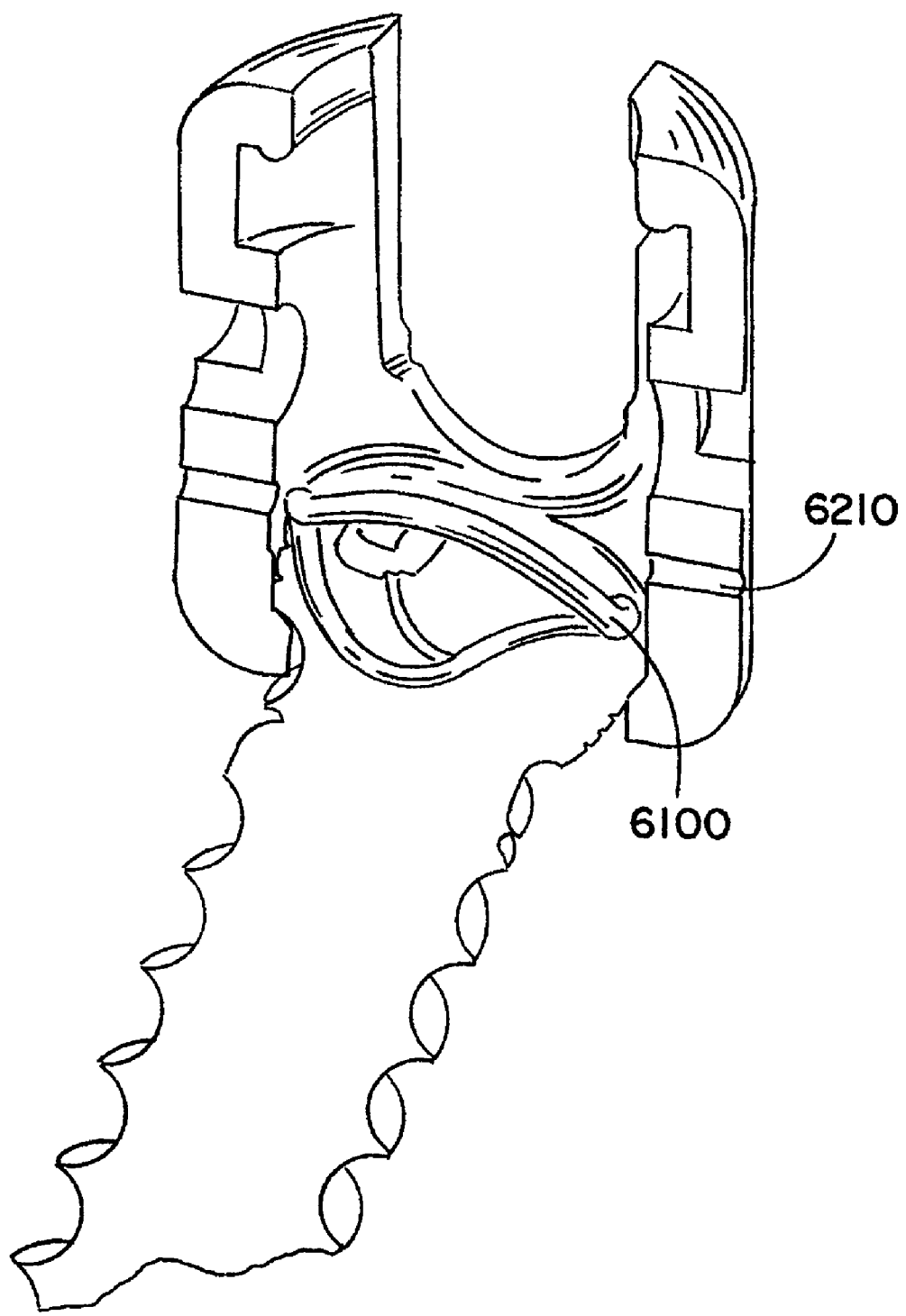
FIG. 62 is a sectional view of the yoke, anvil, and screw showing the placement of the gimble in FIG. 61.

As yet another embodiment, FIG. 58 illustrates cam lock member 5800. This cam lock member comprises a cap body 5810, and preferably one or more flipper bars 5820. During insertion of the cam lock member 5800 into a yoke 5900, the flipper bars 5820 are positioned generally vertical to the axis of insertion into the yoke 5900 such that the cam lock member 5800 can seat in a cap recess 5910. Once fully seated, the flipper bars 5820 rotate outward into the flipper recess 5920. This rotation of the flipper bars 5820 may be caused by action of a deployment spring (not shown) acting on each flipper bar 5820 or by initial rotation of a central cam post 5830. The central cam post 5830 comprises camming lobes which at least block inward rotation of the flipper bars 5820 to prevent the cam lock member 5800 from escaping the cap recess 5910. In addition, in a further embodiment, a central cam post

6010 may be configured to move the flipper bars 6020 lateral within the cap body 6030 to cause an effective lowering of the rod contact portion 6040 and compressing the spinal rod 16 to a fixed position. Derotation of the central cam post 5830, 6010 will release the flipper bars 6020, 5820, such that the cam lock member 5800, 6000 may be removed from the yoke.

As an alternative, cam lock member 5800 may comprise a cap body 5810 which includes a rod locking ramp similar to rod locking ramp 4904 and a central cam post 5830 comprising rod locking lobes similar to rod locking lobes 4720 such that rotation of the central cam post 5830 causes its effective lowering towards the spinal rod 16 and ultimately the fixation of the rod 16. Similarly to the embodiment in FIG. 47, the central cam post 5830 may include a flipper blocking portion similar to bar locking lobes 4722 to keep the flipper bars 6020, 5820 deployed and thereby keeping the cam lock member 5800, 6000 locked within the cap recess 5910.

As discussed and illustrated earlier in FIG. 32, the outer surface 602 of the yoke 512 may include blind apertures or holes 650. The thin wall portion 652 adjacent each blind hole 650 is deformed into the recess 608 so that the screw 502 and anvil 516 subassembly cannot be pulled back out of the yoke 512. Alternatively, a gimble retainer 6100 may be used to secure the screw 502 and anvil 516 subassembly in the yoke 512. The gimble 6100 may have one or more retention tab 6102 portions to secure it in the yoke 512. The yoke preferably includes one or more complementary retention structures 6210. These structures 6210 are preferably round through holes or apertures, however, they may be blind, of other non-circular forms, and be fashioned to be better described as a notch. In any event, the retention structures 6210 serve to hold the retention tab 6102 in position in the yoke 512 while allowing the gimble retainer 6100 to pivot as the head of the screw 536 is polyaxially adjusted within the yoke 512. It is preferred that the gimble 6100 include a spinal rod cup portion 6104 preferably fashioned to the outer profile of the spinal rod 16 such that the spinal rod 16 may rest on the anvil 516 and deep in the yoke channel 601. Notice that the gimble retainer 6200 is sized to fit in the yoke and has a central aperture 6302, preferably round, functioning to provide access for the drive tool to access the screw head notches 560 and for the anvil 516 to access the spinal rod 16. The bottom surface of the rod cup portions 6104 may contact the top surface 550 of the screw head 536. At extreme angles of polyaxial screw 502 motion, the rod cup portion 6104 may be pinched between the top surface 550 and the spinal rod 16. Under such circumstances, the rod cup portion 6104 may experience elastic or plastic deformation especially when the cam locking member is locked. It is preferred that the gimble retainer 6100 be manufactured from a biocompatible material such as titanium or titanium alloys, nitinol, stainless steel, or polymers. Further, the gimble 6100 may be machined, stamped, or pressed during manufacture.

Assembly may involve elastically compressing the gimble retainer 6100 until the retention tabs 6102 are able to pass down the inner surface 624 of each yoke wall 604, 606 above the pre-inserted screw 502 and anvil 516 subassembly. The gimble 6100 is then allowed to uncompress and the retention tab 6102 is directed into the respective retention structure 6210. As an added benefit, this gimble retainer 6100, 6200 keeps the screw head 536 depressed in the throughbore 612 of the yoke thereby minimizing play therebetween. Reduction of this play reduces the difficulty the user experiences when using instruments in combination with the implants.

In other forms of the systems 10, 500, and 4500 described above, the bone anchor member may be provided as a number of variations. For instance, a fixed screw may be employed with the system, either as an integral component with the coupling member or as a component received in the coupling member, as has been described. In the same manner, a hook may be employed with the coupling members.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A spinal fixation system for fixing an elongate member in a desired position relative to a patient's spine, the spinal fixation system comprising:
    an anchor member for being secured to a vertebral bone of the spine;
    a coupling member having an internal space for securing the elongate member relative to the anchor member in the internal space;
    a lock device for being received in the internal space to be operable to be releasably fixed in an initial position in the coupling member prior to operation of the lock device for fixing the elongate member relative to the coupling member;
    opposing lock arms of the lock device operable to retain a cap assembly of the lock device within the internal space of the coupling member; and
    wherein the lock device is arranged and configured to pivot about a pivot axis extending through the lock arms.

2. The spinal fixation system of claim 1, wherein the lock arms include a retracted position so that the cap assembly can be received in the internal space and an extended position for retaining the lock device in the internal space, and wherein the coupling member includes opposing side wall portions and apertures defined therein that are positioned to receive a portion of the lock arms in the extended position.

3. The spinal fixation system of claim 2, wherein the lock device includes a cam post arranged and configured to rotate about a longitudinal axis extending through the internal space and generally transverse to the pivot axis, and wherein rotation of the cam post being operable to move the lock arms to the extended position.

4. The spinal fixation system of claim 3, wherein the opposing side wall portions of the coupling member includes guide slots on an internal surface thereof, the guide slots arranged and configured to guide the lock arms to the apertures.

5. The spinal fixation system of claim 4, further comprising a biasing element for biasing the opposing lock arms into the extended position upon rotation of the cam post.

6. The spinal fixation system of claim 5, wherein the guide slots are substantially J-shaped.

7. The spinal fixation system of claim 5, wherein the lock device includes a locking member configured for engaging the elongate member, and with the lock device in the initial position in the coupling member, the locking member a predetermined gap spacing from the elongate member.

8. A spinal fixation system for fixing an elongate member in a desired position relative to a patient's spine, the spinal fixation system comprising:
    an anchor member for being secured to a vertebral bone of the spine;
    a coupling member having an internal space for securing the elongate member relative to the anchor member in the internal space;
    opposing side wall portions of the coupling member including slot openings therebetween with the elongate member extending through the slot openings and out from either side of the coupling member;

a locking cap for being received in the internal space to be operable to fix the elongate member in the coupling member;

at least one protrusion extending into the internal space from a corresponding one of the opposing side wall portions of the coupling member;

at least one guide track of the locking cap in which the at least one protrusion is received and configured so that turning of the gap causes the elongate member to be fixed in the coupling member;

wherein the at least one guide track is positioned on side wall portions of the locking cap so that the locking cap can be rotated relative to the side wall portions of the coupling member; and wherein the at least one protrusion include an upstanding flange on an end thereof, the upstanding flange cooperating with a downwardly extending lip of the at least one guide track to prevent splaying of the opposing side wall portions.

9. The spinal fixation system of claim 8, wherein the at least one guide track extends partially about the side wall portions and define a stop therein such that rotation of the locking cap is hindered when the at least one protrusion engages the stop.

10. A spinal fixation system for fixing an elongate member in a desired position relative to a patient's spine, the spinal fixation system comprising:

an anchor member for being secured to a vertebral bone of the spine, the anchor member including a head and a shank depending therefrom;

a coupling member having an internal space for securing the elongate member relative to the anchor member in the internal space;

a seat of the coupling member having a through opening sized to allow the shank to pivotally extend therethrough in a plurality of orientations with the head engaged with the seat;

a retainer received in the internal space arranged and configured to minimize pivoting of the coupling member relative to the anchor member and to substantially retain the head of the anchor member against the seat within the internal space to minimize play therebetween; and wherein the retainer comprises a resilient ring member having opposed downwardly extending cupped portions thereof, the cupped portions being arranged and configured for receiving a portion of the elongate member.

11. The spinal fixation system of claim 10, wherein the resilient ring member includes retention tabs and the side wall portions of the coupling member include slots positioned to received the retention tabs therein in order to hold the retainer in the internal space.

* * * * *